United States Patent [19]

Sena et al.

[11] Patent Number: 5,670,316

[45] Date of Patent: *Sep. 23, 1997

[54] DIAGNOSTIC APPLICATIONS OF DOUBLE D-LOOP FORMATION

[75] Inventors: Elissa P. Sena, Palo Alto; Cornelia J. Calhoun, San Francisco; David A. Zarling, Menlo Park, all of Calif.

[73] Assignee: Daikin Industries, Ltd., Osaka, Japan

[*] Notice: The term of this patent shall not extend beyond the expiration date of Pat. No. 5,273,881.

[21] Appl. No.: 199,317

[22] PCT Filed: Sep. 4, 1992

[86] PCT No.: PCT/JP92/01135

§ 371 Date: May 25, 1994

§ 102(e) Date: May 25, 1994

[87] PCT Pub. No.: WO93/05178

PCT Pub. Date: Mar. 18, 1993

Related U.S. Application Data

[63] Continuation-in-part of Ser. No. 910,791, Jul. 9, 1992, abandoned, which is a continuation-in-part of Ser. No. 755,462, Sep. 4, 1991, Pat. No. 5,273,881, which is a continuation-in-part of Ser. No. 520,321, May 7, 1990, Pat. No. 5,223,414.

[51] Int. Cl.[6] .............................. C12Q 1/68; C12Q 1/70; C12P 19/34; C07H 21/04
[52] U.S. Cl. .............................. 435/6; 435/5; 435/91.2; 536/21.3; 536/21.32; 536/21.33
[58] Field of Search .............................. 435/6, 5, 91.2; 536/24.3–0.33

[56] References Cited

U.S. PATENT DOCUMENTS

| 4,563,419 | 1/1986 | Ranki et al. |
| 4,683,195 | 7/1987 | Mullis et al. |
| 4,683,202 | 7/1987 | Mullis. |
| 4,766,062 | 8/1988 | Diamond et al. |
| 4,888,274 | 12/1989 | Radding et al. |
| 5,273,881 | 12/1993 | Sena et al. ............................... 425/6 |

FOREIGN PATENT DOCUMENTS

| 0164876 A | 5/1985 | European Pat. Off. |
| 0164876 B | 5/1985 | European Pat. Off. |
| 0322311 | 12/1988 | European Pat. Off. |
| 0328829 A | 12/1988 | European Pat. Off. |
| WO85/05685 | 5/1985 | WIPO. |
| WO87/01730 | 3/1987 | WIPO. |
| WO91/17267 | 11/1991 | WIPO. |

OTHER PUBLICATIONS

Cheng, S., et al., "Use of Psoralen–modified oligonucleotides to Trap Three–stranded RecA–DNA Complexes and Repair of These Cross–linked Complexes by ABC Excinuclease," *J. Biol. Chem.* 263: 15110 (1988).

Cheng, S., et al., "RecA–Directed Hybridization of Psoralen–Monoadducted DNA oligonucleotides to Duplex Targets," in *Photo–chemical Probes in Biochemistry* (P.E. Nielsen, ed.), pp. 169–177 (1989).

Conney, M., et al., "Site–Specific Oligonucleotide Binding Represses Transcription of the Human c–myc Gene in Vitro," *Science* 241: 456–459 (1988).

Cox, M.M., et al., "Enzymes of General Recombination," *Ann. Rev. Biochem.* 56: 229–262 (1987).

Dervan, P.B., "Design of Sequence–Specific DNA–Binding Molecules," *Science* 232: 464–471 (1986).

(List continued on next page.)

*Primary Examiner*—W. Gary Jones
*Assistant Examiner*—Dianne Rees
*Attorney, Agent, or Firm*—Gary R. Fabian; Carol A. Stratford; Peter J. Dehlinger

[57] ABSTRACT

The present invention describes the formation of RecA protein catalyzed double-stranded probe:duplex linear target DNA complexes that are stable to deproteinization. The uses of this stable probe:target complex in diagnostic/DNA detection systems in in vitro and in situ DNA hybridization reactions is discussed. The probe:target complexes are also useful for diagnostic application in RecA protein facilitated DNA amplification reactions.

21 Claims, 17 Drawing Sheets

OTHER PUBLICATIONS

Ferrin, L.J., and Camerini–Otero, R.D., "Selective Cleavage of Human DNA: RecA–Assisted Restriction Endonuclease (RARE) Cleavage," *Science* 254: 1494–1497 (1991).

Francois, J.–C., et al., "Sequence–specific recognition and cleavage of duplex DNA via triple–helix formation by oligo–nucleotides covalently linked to a phenanthroline–copperchelate," *Proc. Natl. Acad. Sci. USA* 86: 9702–9706 (1989).

Francois, J.–C., et al., "Inhibition of Restriction Endo–nuclease Cleavage via Triple Helix Formation by Homopyrimidine Oligonucleotides," *Biochem.* 28: 9617–9619 (1989).

Gonda, D.K., et al., "By Searching Processively RecA Protein Pairs DNA Molecules That Share a Limited Stretch of Homology," *Cell* 34: 647–654 (1983).

Hanvey, J.C., et al., "Site–specific inhibition of EcoRI restriction/modification enzymes by a DNA triple helix," *Nucleic Acids Res.* 18(1): 157 (1989).

Hsieh, P., et al., "Pairing of homologous DNA sequences by proteins: evidence for three–stranded DNA," *Genes Dev.* 4: 1951 (1990).

Leahy, M.C., et al., "Topography of the Interaction of recA Protein with Single–stranded Deoxyoligonucleotides," *J. Biol. Chem.* 261: 6954 (1986).

Madiraju, M.V.V.S., et al., "Properties of a mutant recA–encoded protein reveal a possible role for *Escherichia coli* recF–encoded protein in genetic recombination," *Proc. Natl. Acad. Sci. USA* 85: 6592–6596 (1988).

Maher III, L.J., et al., "Inhibition of DNA Binding Proteins by Oligonucleotide–Directed Triple Helix Formation," *Science* 245: 725–730 (1989).

Menetski, J.P., and Kowalczykowski, S.C., "Enhancement of *Escherichia coli* RecA Protein Enzymatic Function by dATP," *Biochem.* 28: 5871–5881 (1989).

Morrison, L.E., et al., "Solution–phase detection of polynucleotides using interacting fluorescent labels and competitive hybridization," *Anal. Biochem.* 183(2): 231–244 (1989) (Medline Abstract No. 07257919 90164919).

Moser, H.E., and Dervan, P.B., "Sequence–Specific Cleavage of Double Helical DNA by Triple Helix Formation," *Science* 238:645–650 (1987).

Radding, C.M., et al., "Homologous Pairing and Strand Exchange in Genetic Recombination," *Ann. Rev. Genet.* 16: 405 (1983).

Rigas, B., et al., "Rapid plasmid library screening using RecA–coated biotinylated probes," *Proc. Natl. Acad. Sci. USA* 83:9591 (1986).

Roca, A.I., et al., "The RecA Protein: Structure and Function," *Crit. Rev. Biochem. Molec. Biol.* 25: 415 (1990).

Shibata, T., et al., "Purified *Escherichia coli* recA Protein catalyzed homologous pairing of superhelical DNA and single–stranded fragments," *Proc. Natl. Acad. Sci. USA* 76: 1638 (1979).

```
7131
        10         20         30         40         50         60         70
5'GATGAGTTCG TGTCCGTACA ACTGGGCGTAA TCATGGCCCT TCGGGGCCAT TGTTTCTCTG TGGAGGAGTC 80         90        100        110        120        130        140
CATGACGAAA GATGAACTGA TTGCCCGTCT CCGCTCGCTG GGTGAACAAC TGAACCGTGA TGTCAGCCTG 150        160        170        180        190        200        210
ACGGGGACGA AAGAAGAACT GGCGCTCCGT GTGGCAGAGC TGAAAGAGGA GCTTGATGAC ACGGATGAAA 220        230        240        250        260        270        280
CTGCCCGGTCA GGACACCCCT CTCAGCCGGG AAAATGTGCT GACCGGACAT GAAAATGAGG TGGGATCAGC 290        300        310        320        330        340        350
GCAGCCGGAT ACCGTGATTC TGGATACGTC TGAACTGGTC ACGGTCGTGG CACTGGTGAA ▼GCTGCATACT 360        370        380        390        400        410        420
GATGCACTTC ACGCCACGCG GGATGAACCT GTGGCATTTG TGCTGCCGGG AACGGGCGTTT CGTGTCTCTG 430        440        450        460        470        480        490
ᵡCGGTGTGGC AGCCGAAAATG ACAGAGCCGG GCCTGGCCAG AATGCAATAA CGGGAGGCGC TGTGGCTGAT 500        3'
TTCGATAACC   7630
```

▼ = Alu I site
ᵡ = Hpa II site

Fig. 2

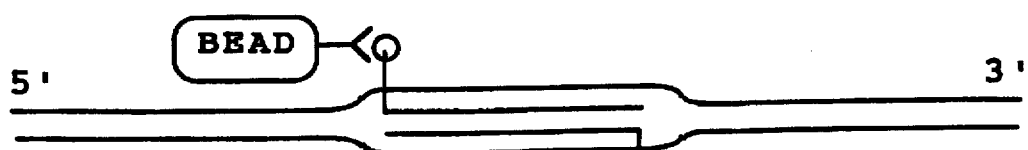
Fig. 10A   O: CAPTURE
           X: REPORTER
Fig. 10B
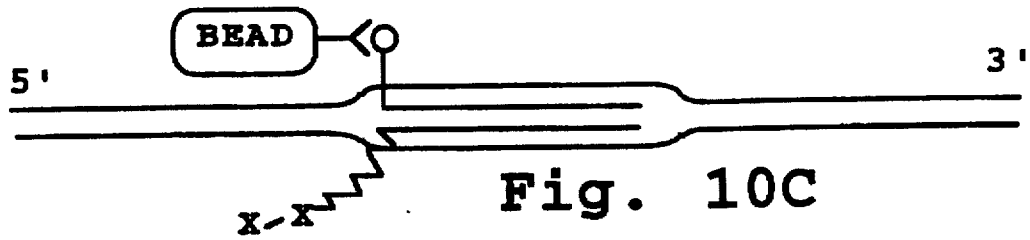
Fig. 10C
Fig. 11A
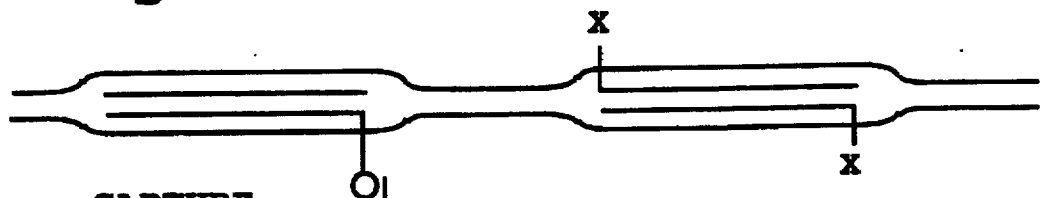
O: CAPTURE
X: REPORTER
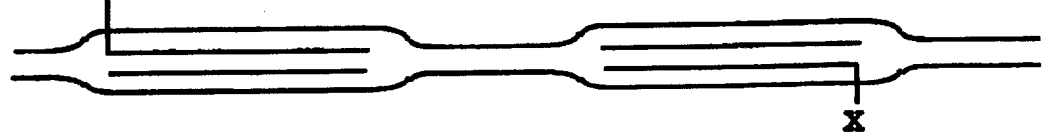
Fig. 11B

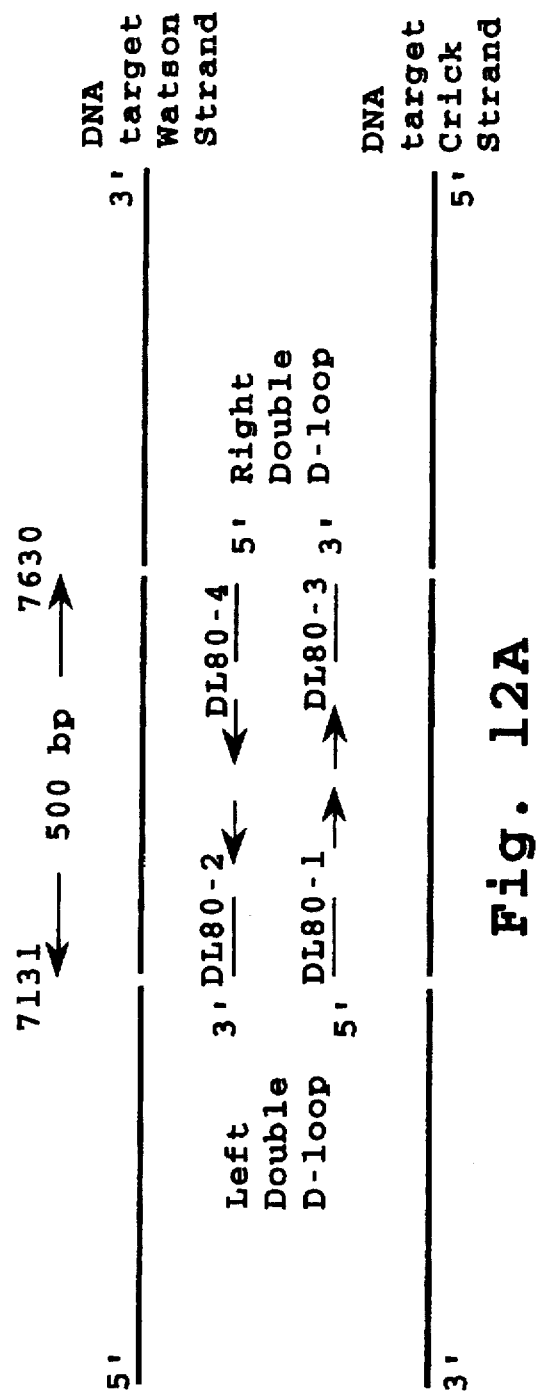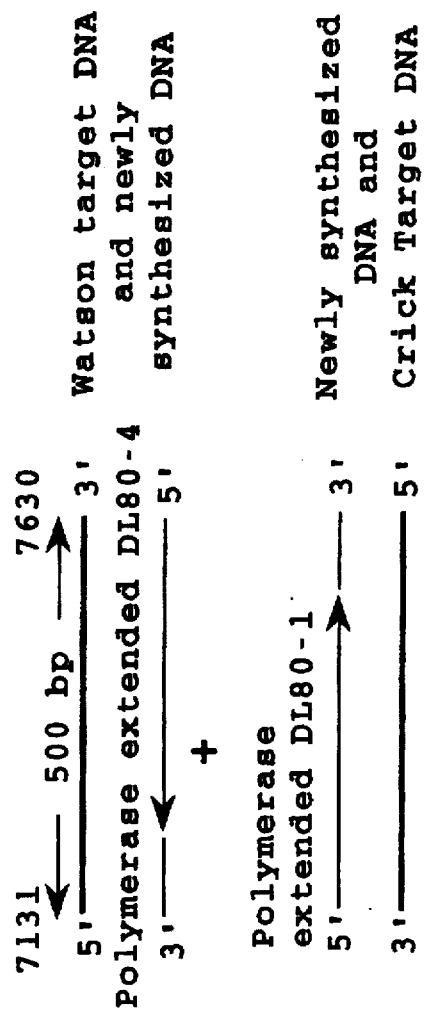
Fig. 12A
Fig. 12B

| DESCRIPTION OF ASSAY STEPS | BASIC REACTIONS |
|---|---|
| Formation of probe: target hybrids | |
| Capture of homologous duplex target DNA on beads | |
| Removal of non-hybridized DNA by washing | |

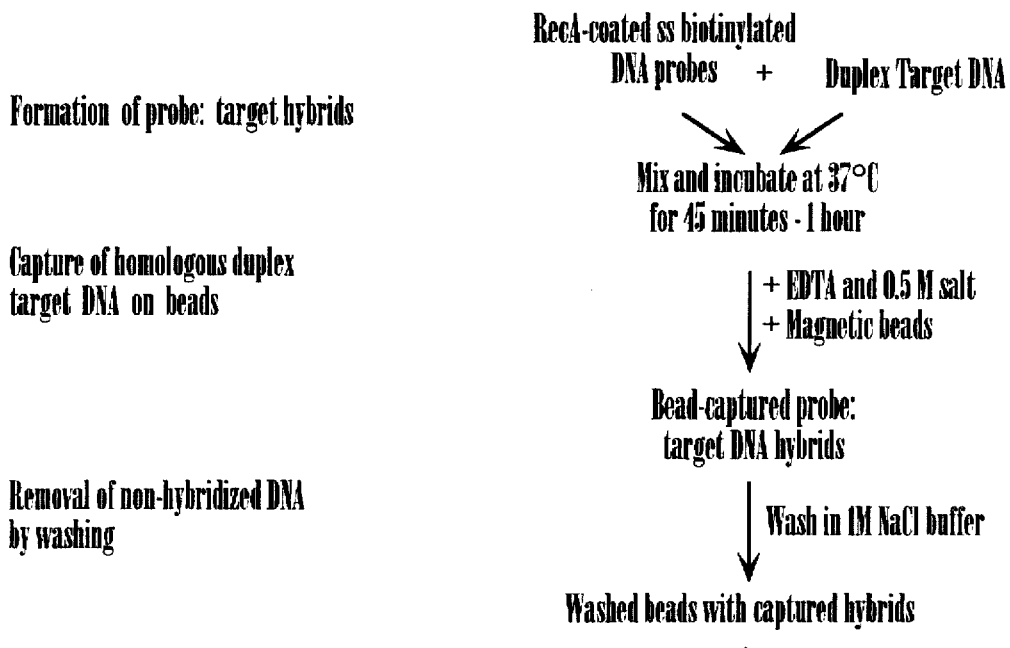

Fig. 20A

| | |
|---|---|
| Target signal amplification | |
| 1. Anneal target with primer(s)* | |
| 2. Extend primer(s) with DNA polymerase to incorporate biotinylated nucleotide(s) | |
| *non-homologous to probe DNA, homologous to desired target DNA | |

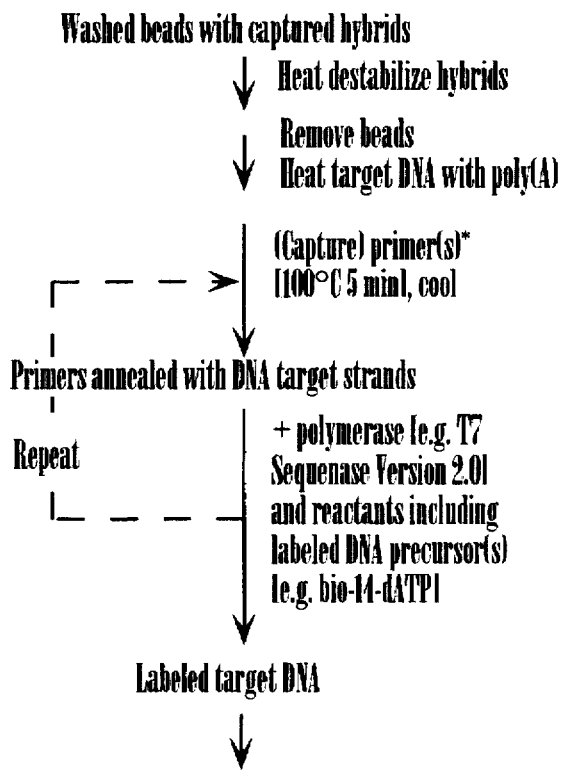

Fig. 20B

DIAGNOSTIC APPLICATIONS OF DOUBLE D-LOOP FORMATION

This application is a continuation-in-part of co-owned, U.S. application Ser. No. 07/910,791, filed 9 Jul. 1992, now abandoned which is a continuation-in-part of co-owned, U.S. application Ser. No. 07/755,462, now U.S. Pat. No. 5,273,881 filed 4 Sep. 1991, which is a continuation-in-part of co-owned, U.S. application Ser. No. 07/520,321, now U.S. Pat. No. 5,223,414 filed 7 May 1990.

FIELD OF THE INVENTION

The present invention relates to the formation of RecA-catalyzed stable double D-loop structures that can be utilized in a variety of diagnostic methods including two probe capture/detection systems, RecA-facilitated DNA amplification, and in situ hybridization.

REFERENCES

Ausubel, F. M., et al., *Current Protocols in Molecular Biology*, John Wiley and Sons, Inc., Media PA.
Bryant, F. R., et al., Proc. Natl. Acad. Sci. U.S.A. 82:297 (1985).
Cassuto, E., et al., Mol. Ge. Genet. 208:10 (1987).
Chen, T. R., Cytogenet. Cell. Genet. 48:19–24 (1988).
Cheng, S., et al., J. Biol. Chem. 263:15110 (1988).
Cheng, S., et al., Photochemical Probes in Biochemistry (P. E. Nielsen, ed.), pages 169–177 (1989).
Corey, D. R., et al., Science 238:1401 (1987).
Cox, M. M. et al., Ann. Rev. Biochem. 56:229–262 (1987).
Davis, L. G., et al., *Basic Methods in Molecular Biology*, Elsevier Publishing Co. (1986).
Dreyer, G. B., et al., Proc. Natl. Acad. Sci. U.S.A. 82:968 (1985).
Eisen, J., et al., Proc. Natl. Acad. Sci. U.S.A. 85:7481 (1988).
Fey, M. F., Schweiz. Med. Wochenschr. 120(20):731–737 (1990).
Fishel, R. A., et al., Proc. Natl. Acad. Sci. U.S.A. 85:3683 (1988).
Fugisawa, H., et al., Nucleic Acids Res. 13:7473 (1985).
Ganea, D., et al., Mol. Cell Biol. 7:3124 (1987).
Gonda, D. K., et al., Cell 34:647–654 (1983).
Griffith, J., et al., Biochem 24:158 (1985).
Halbrook, J., et al., J. Biol. Chem. 264:21403 (1989).
Harlow, E., et al., *Antibodies: A Laboratory Manual*, Cold Spring Harbor Laboratory Press (1988).
Haase, A. T., et al., Proc. Natl. Acad. Sci. U.S.A. 87:4971 (1990).
Hsieh, P., et al., Genes Dev. 4:1951 (1990).
Hsieh, P., et al., J. Biol. Chem. 264:5089 (1989).
Hsieh, P., et al., Cell 44:885 (1986).
Keene, K. et al., Nucleic Acid Res. 12:3057 (1984).
Kemp, D. J., et al., PCT International Application, International Publication No. WO 90/06374 (Application No. PCT/AU89/00526), 14 Jun. 1990.
Kimeic, E. B., Cell 44:545 (1986).
Kimeic, E. B., Cold Spring Harbor Symp. 48:675 (1984).
Kingston, H. M., B. M. J. 299(6690):34–37 (1989).
Kolodner, R. et al., Proc. Natl. Acad. Sci. U.S.A. 84:5560 (1987).
Leahy et al., J. Biol. Chem. 261:6954 (1986).
Lowenhaupt, K., et al., J. Biol. Chem. 264:20568 (1989).
Madiraju, M. V. V. S., et al., Proc. Natl. Acad. Sci. U.S.A. 85:6592 (1988).
Maniatis, T., et al. *Molecular Cloning: A Laboratory Manual*, Cold Spring Harbor Laboratory (1982).
McCarthy, J., et al., Proc. Natl. Acad. Sci. U.S.A. 85:5854 (1988).
McEntee, K., et al., J. Biol. Chem. 256:8835 (1981).
Moore, S. P., et al., J. Biol. Chem. 19:11108 (1990).
Morrical, S. W., et al., Biochem. 29:837 (1990).
Moser, H. E., et al., Science 238:645 (1987).
Mullis, K. B., U.S. Pat. No. 4,683,202, issued 28 Jul. 1987.
Mullis, K. B., et al., U.S. Pat. No. 4,683,195, issued 28 Jul. 1987.
Nelson, M., et al., Nucl. Acids Res. 17:389 (1989).
Olson, M., et al., Science 245, 1434–1435 (1989)
Radding, C. M., Ann. Rev. Genet. 16:405 (1982) 25:1990.
Rigas, B., et al., Proc. Natl. Acad. Sci. U.S.A. 83:9591 (1986).
Roca, A. I., et al., Crit. Rev. Biochem. Molec. Biol. 25:415 (1990).
Saiki, R. K., et al., Proc. Natl. Acad. Sci. U.S.A. 86:6230 (1989).
Sambrook, J., et al., In *Molecular Cloning: A Laboratory Manual*, Cold Spring Harbor Laboratory Press, Vol. 2 (1989).
Scharf, S. J., et al., Science 233:1076–1078 (1986).
Shibata, T., et al, Proc. Natl. Acad. Sci. U.S.A. 76:1638 (1979).
Shibata, T., et al., J. Biol. Chem. 256:7557 (1981).
Sluka, J. P., et al., Science 238:1129 (1987).
Strickler, J. G., et al., Am. J. Clin. Pathol. 93(4 Suppl. 1):S44–8 (1990).
Sugino, A., et al., Proc. Natl. Acad. Sci. U.S.A. 85:3683 (1988).
Trask, B., et al., Hum. Genet. 78:251 (1988).
van Dekken, H., et al., Cytometry 11:153 (1990).
van Dekken, H., et al., Cytometry 11:579 (1990).
Wachsmuth, K., Rev. Infect. Dis. 8(5):682–692 (1986).
Weier, H-U. G., et al., J. Histochem. and Cytochem. 38:421 (1990).
Woodbury, C. P., et al., Biochemistry 22(20):4730–4737 (1983).
Zlvin, R. A., et al., European Patent Application No. 88307793.5, Publication No. 0 305 145, 1 Mar. 1989.

BACKGROUND OF THE INVENTION

RecA+ protein (wild type) is a 37,842 dalton protein found in the bacterium *Escherichia coli*, which is important for homologous DNA recombination. Most information about its biochemistry and enzymology comes from in vitro studies using purified RecA+ protein. Numerous in vitro studies have shown that RecA+ protein is intimately involved in the pairing reaction between homologous DNA sequences that ultimately leads to homologous recombination events (Radding; see Cox et al. or Roca et al. for recent reviews of RecA+ protein properties). It is this pairing reaction that makes RecA+protein highly useful for DNA diagnostics applications.

In the presence of ATP, RecA+ protein catalyzes strand exchange between a number of substrates, the most relevant for DNA probe applications being single- and double-stranded DNAs. RecA protein coated single-stranded DNA probes interact with the homologous portion of a double-stranded ("native") target sequence initially by forming a recombination intermediate containing hybridized, partially joined molecules called (single) D-loops (or in some cases triple-stranded structures) (Shibata et al., 1979). This is followed by branch migration, and forming of fully hybrid molecules between the original single- and double-stranded DNAs, depending upon the extent of their homology.

Short displacement loops or triple-stranded D-loop structures in linear targets are usually unstable after deproteinization. RecA protein has been shown to form stable complexes with short oligonucleotides, between 9 and 20 bp (or larger) in length, in the presence of ATPγS and excess RecA protein (Leahy et al.). When linear double-stranded targets are used, stable probe target pairing after RecA removal appears to require (i) a homologous region of at least 38 to 56 bp, and (ii) the location of the probe target homology at the end of the linear duplex (Hsieh et al. 1990; Gonda et al.).

Rigas et al. reported that a single-stranded 43-mer could form a single D-loop complex stable to deproteinization when double-stranded negatively supercoiled circular plasmid DNA was used as the target.

When a double-stranded negatively supercoiled circular target DNA is used, RecA coated single-stranded oligonucleotide probes can also be stabilized by psoralen crosslinking before removal of the RecA protein: probe-target single D-loop products can be recovered if the oligos are at least 30-mer size (Cheng et al., 1989). To obtain psoralen crosslink stabilized single D-loop probe-target complexes when double-stranded linear DNA duplexes are used as target DNA, the probes must be at least 80 to 107-mer size (Cheng et al., 1988): these reactions are very low efficiency when compared to similar reactions with negatively supercoiled circular targets.

Experiments performed in support of the present invention have demonstrated that probe:target DNA complexes, which are stable to deproteinization, can be generated in RecA protein catalyzed reactions providing that duplex probes, which contain sequences complementary between probe-strands, are used in the hybridization reactions. This discovery provides a number of opportunities for diagnostic application that exploit this stable RecA protein catalyzed probe:target hybridization complex.

SUMMARY OF THE INVENTION

The present invention includes a diagnostic method for detecting a linear duplex DNA analyte, having first and second strands, where the analyte contains a first internal DNA target sequence. The method teaches providing a set of two DNA probes that each contain sequences complementary to the first target sequence strand or the second target sequence strand, where these probes also have a region of complementary overlap to each other. Both probe strands are then coated with RecA protein in a RecA protein coating reaction. The RecA coated probes are combined with the linear duplex DNA, which contains the target sequence, under conditions that produce a probe:target complex. This probe:target complex contains both probe strands and both strands of the linear duplex analyte. The probe:target complex is stable to deproteinization, although in the method of the present invention it is not necessarily deproteinized. The presence of the probe DNA in the probe:target complex is then detected.

In one embodiment of the invention the RecA protein is the wild-type RecA protein of *Escherichia coli*. Alternatively, the RecA protein can be the mutant recA-803 protein of *Escherichia coli* or a RecA-like protein from a number of sources.

The RecA-protein coating reactions of the present invention can be carried out using a variety of co-factors, including ATPγS, rATP (alone and in the presence of a regenerating system), dATP, GTPγS, and mixes of ATPγS and rATP, and ATPγS and ADP.

In one embodiment of the invention, the region of complementary overlap between the probe strands is at least about 78 base pairs and less than about 500 base pairs. The probe strands may also contain an end terminal extension of DNA that is not complementary to either target strand. When both strands contain such an end terminal extension, these DNA extensions may be complementary to each other.

One way in which to accomplish the detecting of the method of the present invention is by deproteinization of the probe:target complex, followed by electrophoretic separation of the probe:target complex from free probe. The probe:target complex can be deproteinized by a variety of methods including treatment with SDS or proteinase K, as well as standard chemical deproteinization methods, such as phenol-based methods. Alternatively, the detecting can include the use of a capture system that traps the probe:target complex, where the first probe strand is labeled with a capture moiety and the second probe strand is labeled with a detection moiety. For example, one probe strand can be biotin labeled and the other digoxigenin labeled. The probe:target complex can then be captured/detected using solid support-streptavidin (or avidin)/labeled anti-digoxigenin, or solid support-anti-digoxigenin antibody/labeled streptavidin (or avidin). In a different embodiment, the first probe strand contains a capture moiety and the second probe strand contains a radioactive label to be used for detection.

The probe strands can be labelled for capture in a number of ways, for example, using biotin or digoxigenin attached to the probe and streptavidin (or avidin) or an anti-digoxigenin antibody, respectively, for capture. The probe strands can also be labelled for detection using a number of different moieties including: radioactive, biotin, digoxigenin. Radioactive labels can be identified by, for example, autoradiography or scintillation counting. The presence of biotin or digoxigenin can be detected by streptavidin or an anti-digoxigenin antibody, respectively, where the streptavidin (or avidin) or anti-digoxigenin is radioactively labeled, enzyme labeled (e.g., alkaline phosphatase, peroxidase, beta-galactosidase or glucose oxidase) or fluorochrome-labeled (e.g., fluorescein, R-phycoerythrin, or rhodamine). Detection of the probe strands in the probe:target complex can also be accomplished by DNA polymerase facilitated primer extension from the 3'-ends of each probe strand, where the primer extension is performed in the presence of all four dNTPs and one or more dNTP contains a detectable moiety.

The method of the present invention further includes providing a second set of two DNA probes, having first and second strands, complementary to a second duplex target sequence, where the first strand of the probe contains sequences complementary to one strand of the second target sequence and the second strand of the probe contains sequences complementary to the other strand of the second target sequence, where (i) these probes also have a region of complementary overlap to each other, and (ii) the second set of probes does not hybridize to the first set of probes. The two probe sets are coated with RecA protein in a RecA protein coating reaction. The RecA coated probe sets are combined with the linear duplex DNA, containing the two target sequences. The combining is done under conditions that produce probe:target complexes which contain all four probe strands. The resulting probe:target complex is stable to deproteinization. The presence of the probe DNA is then detected in the probe:target complexes.

The method involving two probe sets can be utilized in many of the same ways as described above for a single probe set. For example, the first probe set can be labeled with a capture moiety and the second probe set labeled with a detection moiety.

The double-stranded probe:duplex target complexes involving two probe sets can also be used in a RecA protein facilitated DNA amplification method. For example, the two probe sets can be hybridized to their duplex target sequences in the presence of ATPγS [or rATP (with or without a suitable ATP regeneration system), dATP, and mixtures of ATPγS and ADP] and reacted in a reaction mixture also containing, all four dNTPs, RecA protein and DNA polymerase. This reaction is performed below the temperature required for thermal dissociation of the two target strands and continued until a desired degree of amplification of the target sequence is achieved. The amplification reaction may further include repeated additions of (i) DNA polymerase and (ii) RecA protein-coated probes during the course of the amplification reaction. Other approaches to amplification, which can be applied to the present invention, have been set forth in co-pending U.S. application Ser. No 07/520,321, filed 7 May 1990. In each probe set, the 3' end of one strand will be internal to the region defined by the two primer sets: these ends are necessary for the amplification reaction. However, the opposite 3'ends of each primer pair, external to the region defined by the two primer sets, can be blocked to inhibit the formation of extension products from these ends. This amplification method can also be used as a detection method, where detection of the probe in the probe:target complex is accomplished by DNA polymerase facilitated primer extension from the 3'-ends of each probe strand, where the primer extension reaction is performed in the presence of all four dNTPs and one or more dNTP contains a detectable moiety.

The double-stranded probe:duplex target complexes can also be used to block cleavage of any targeted restriction site. Blocking cleavage can be accomplished in a number of ways including: (i) forming the probe:target complex and treating with the restriction enzyme before deproteinization of the complex; (ii) using methylated or un-methylated probes, depending on the sensitivity of a selected enzyme to the presence of methyl groups; and (iii) introducing a sequence mismatch in each strand of the probe, which, when the probe hybridizes to the target, eliminates the restriction site.

The double-stranded probe:duplex target complexes can also be used to generate site specific cleavage of double-stranded target DNA. The double-stranded probe can be modified with moieties capable of cleaving each strand of the target duplex: this probe modification can take place before or after deproteinization depending of the nature of the cleaving moiety. Examples of such moieties are iron FeII (for iron/EDTA facilitated cleavage), non-specific phosphodiesterases, and restriction endonucleases. In either case, cleavage specificity is conferred by the target sequence which is defined by the double-stranded oligonucleotide probe.

Both the restriction site protection method and the site specific cleavage method are useful in restriction fragment length polymorphism analysis.

Another embodiment of the present invention includes a method for isolating a linear duplex DNA analyte, having first and second strands, containing a first internal DNA target sequence, where the duplex DNA analyte is present in a mixture of nucleic acid molecules. In this method a set of two DNA probes is provided, having first and second probe strands, where the first and second probe strands (i) contain complementary sequences to the first and second target sequence strands, and (ii) where these complementary sequences also contain complementary overlap between the probe strands. The probes are then coated with RecA protein. The coated probes are combined with the linear duplex DNA, which contains the target sequence, under conditions that produce a probe:target complex containing the probe strands and both target strands: the resulting probe:target complex is stable to deproteinization. The probe:target complex is separated from the mixture of nucleic acid molecules. The duplex DNA analyte, which contains the target sequence, is then isolated.

In this method, the complex can be separated from the nucleic acid mixture using, for example, probes containing biotin moieties that are captured with streptavidin or avidin. The streptavidin or avidin can be bound to a solid support, such as paramagnetic beads.

The method further includes heat denaturation of the isolated probe:target complex at a temperature (i) sufficient to release the duplex DNA analyte containing the target sequence from the complex, and (ii) below the melting temperature of the duplex DNA analyte containing the target sequence. This allows the isolation of intact duplex molecules. The duplex can then be denatured to single-strands if so desired. Alternatively, the complex can be heat denatured at a temperature (i) sufficient to release the duplex DNA analyte containing the target sequence from the complex, and (ii) at or above the melting temperature of the duplex DNA analyte containing the target sequence. This results in the isolation of single-stranded DNA molecules derived from the captured duplex.

Another embodiment of the present invention is a method for detecting a linear duplex DNA analyte in a mixture of nucleic acid molecules. The method includes isolating the linear duplex DNA analyze as described above and obtaining single-stranded DNA molecules derived from duplex DNA analyte: this is typically accomplished by heating the duplex above the melting temperature of the duplex (heat denaturation). To the single-stranded target DNA analyte molecules, at least one DNA synthesis primer is added that is complementary to the target sequence and that does not contain sequences which were present in either of the two original DNA probes. Detection of the DNA analyte is accomplished by DNA polymerase facilitated primer extension from the 3'-end of the primer, wherein the primer extension is performed in the presence of all four dNTPs and at least one dNTP contains a detectable moiety.

The double-stranded probe:duplex target complexes of the present invention can also be used for diagnostic in situ detection techniques.

BRIEF DESCRIPTION OF THE FIGURES

FIG. 2 presents the nucleotide sequence of a 500 bp lambda genomic region: this sequence is also presented as SEQ ID NO:1.

FIG. 6B illustrates that two DNA probe strands are necessary for the production of stable, deproteinized, RecA protein catalyzed hybridization complexes.

FIGS. 10A, 10B, and 10C illustrate several detection systems based on a single double-stranded probe:duplex linear target DNA complex.

FIGS. 11A and 11B illustrate several detection systems based on a multiple double-stranded probe:duplex linear target DNA complex.

FIG. 12 shows RecA-protein catalyzed two-double D-loop primer positioning on native target DNA (FIG. 12A) and DNA amplification with ligation wise followed by ligation with DNA ligase (in the absence of primer/probe displacement) (FIG. 12B).

In FIG. 13, X and X' can be the same or different: for example X can be radioactively labeled and X' can carry a digoxigenin moiety.

FIGS. 20A, 20B, and 20C show a schematic outline of a homogeneous diagnostic assay for duplex DNA target with Double-D-loop hybrids.

DETAILED DESCRIPTION OF THE INVENTION

I. Generation of RecA Catalyzed Probe:Target Hybridization Complexes Which are Stable to Deproteinization.

A. DNA probes and primers.

Figure 1:
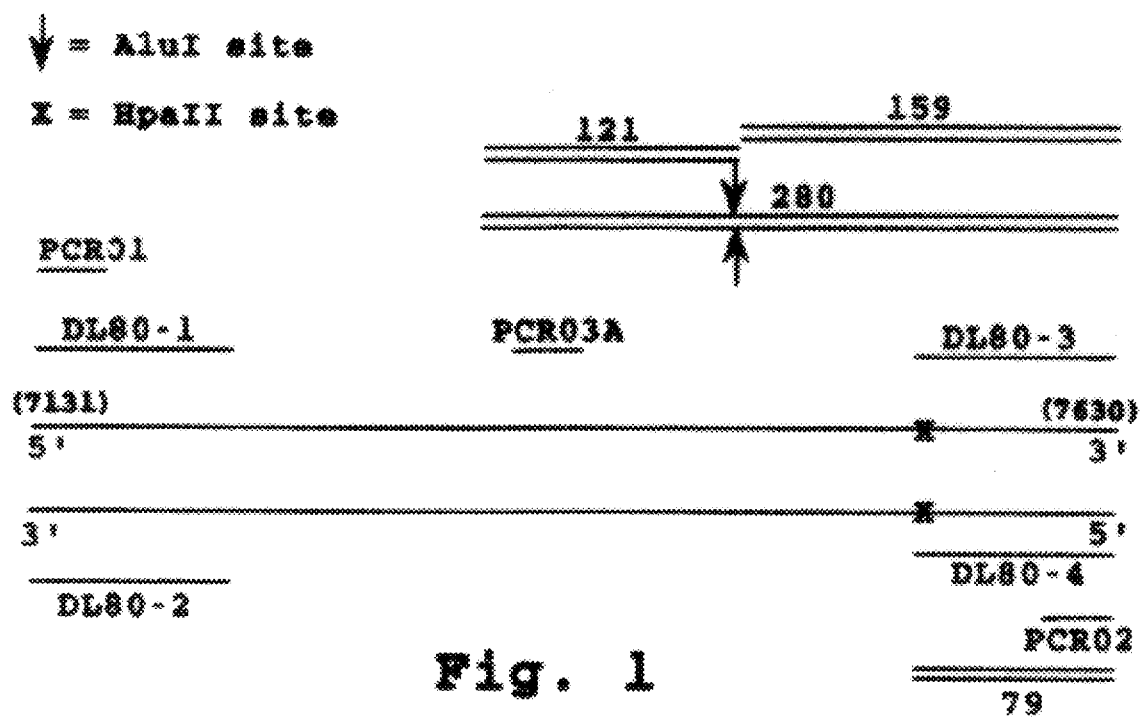
FIG. 1 illustrates the relationships of the probes and primers, listed in Table 1, to the lambda genome.

Experiments performed in support of the present invention show that short double-stranded DNA molecules or complementary single-stranded molecules can be used to generate hybridization complexes with linear target DNA molecules at internal regions and these complexes are stable to deproteinization. As an example of these stable hybridization complexes, double-stranded and complementary single-stranded DNA molecules of varying lengths were prepared for use as probes and primers (Example 1, Table 1). These DNA molecules were chosen to have homology to various portions of a 500 bp region of the lambda phage genome. The relationships of the probes and primers, listed in Table 1, to the lambda genome is illustrated in FIG. 1. The nucleotide sequence of the 500 bp lambda genomic region is presented in FIG. 2.

B. Preparation of RecA protein and Probe Coating.

In the present invention RecA protein refers to a family of RecA-like recombination proteins all having essentially all or most of the same functions, particularly: (i) the protein's ability to properly position primers on their homologous targets for subsequent extension by DNA polymerases; (ii) the ability of RecA protein to topologically prepare DNA for DNA synthesis; and, (iii) the ability of RecA protein/DNA primer complexes to efficiently find and bind to complementary sequences. The best characterized RecA protein is from *E. coli*; in addition to the wild-type protein a number of mutant RecA-like proteins have been identified (e.g. recA-803, Madiraju, et al.). Further, many organisms have RecA-like strand-transfer proteins (e.g., Fugisawa, H., et al.; Hsieh, P., et al., 1986; Hsieh, P., et al., 1989; Fishel, R. A., et al.; Cassuto, E., et al.; Ganea, D., et al.; Moore, S. P., et al.; Keene, K., et al.; Kimeic, E. B., 1984; Kimeic, E. B., 1986; Kolodner, R., et al.; Sugino, A., et al.; Halbrook, J., et al.; Eisen, A., et al.; McCarthy, J., et al., Lowenhaupt, K., et al.)

RecA protein is typically obtained from bacterial strains that overproduce the protein: Example 2 describes the purification of wild-type *E. coli* RecA protein and mutant recA-803 protein from such strains. Alternatively, RecA protein can also be purchased from, for example, Pharmacia (Piscataway N.J.).

Figure 18:
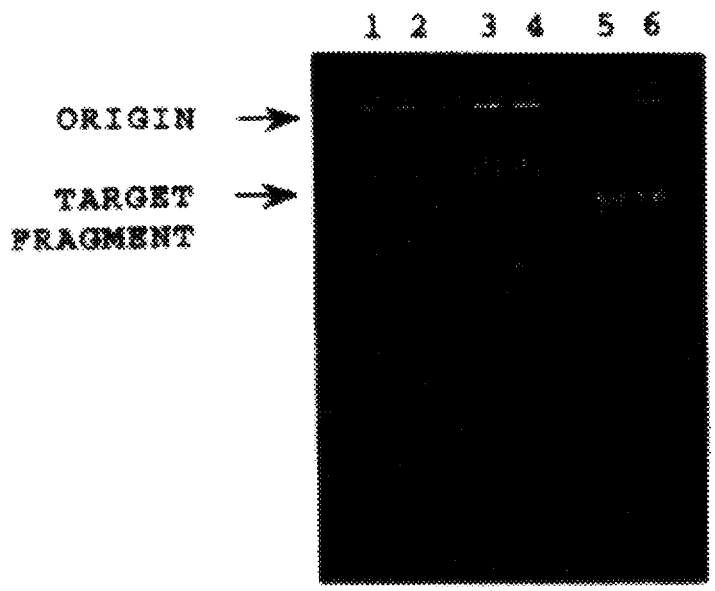
FIG. 18 shows an ethidium bromide strained agarose gel on which the components of deproteinized RecA mediated double D-loop hybridization reactions, using heat denatured 500-mer probe and ATPγS and ATPγS/rATP mixes as cofactors, were resolved by electrophoresis.
Figure 19:
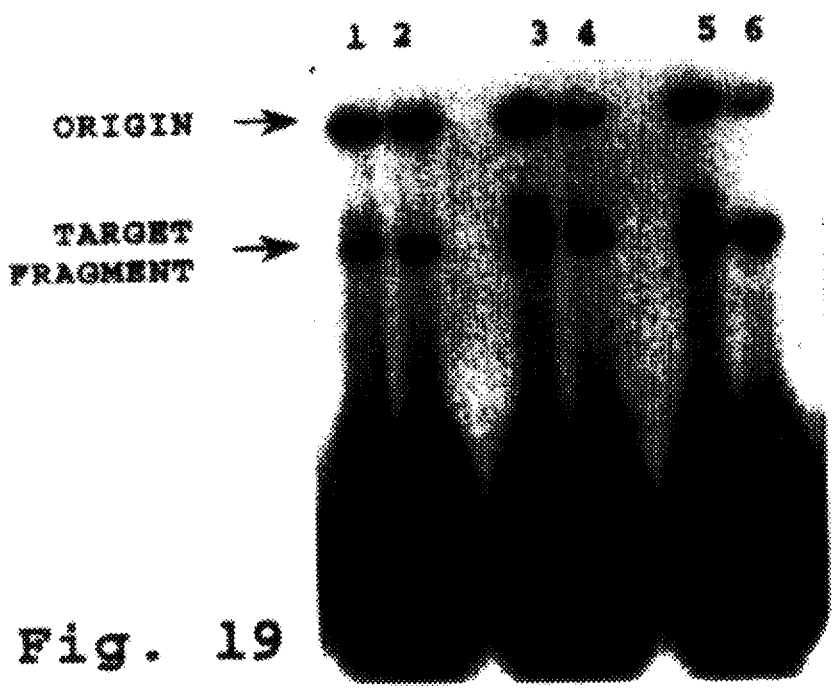
FIG. 19 shows an autoradiogram of the gel shown in FIG. 18, after drying.

The conditions used to coat DNA probes with RecA protein and ATPγS are described in Example 3. Alternatively, probes can be coated using GTPγS, rATP (alone or in the presence of a rATP regenerating system (Boerhinger Mannheim)), dATP, mixes of ATPγS and rATP, or mixes of ATPγS and ADP. The use of ATPγS, rATP, dATP and GTPγS as cofactors in the RecA protein coating reaction is described in Example 10. The results of double D-loop complex formation using these cofactors are presented in FIGS. 16 and 17. FIG. 17 shows that in the presence of each of ATPγS, rATP, dATP and GTPγS double D-loop hybridization complexes, which are stable to deproteinization, were formed. Further, Example 11 describes the use of mixtures of ATPγS/rATP as cofactors for the RecA protein coating reactions. The results shown in FIGS. 18 and 19 show that in the presence of such mixtures double D-loop hybridization complexes, which are stable to deproteinization, were formed. In addition to ATPγS/rATP, mixtures of other cofactors also work in the RecA protein coating reaction.

Figure 3:
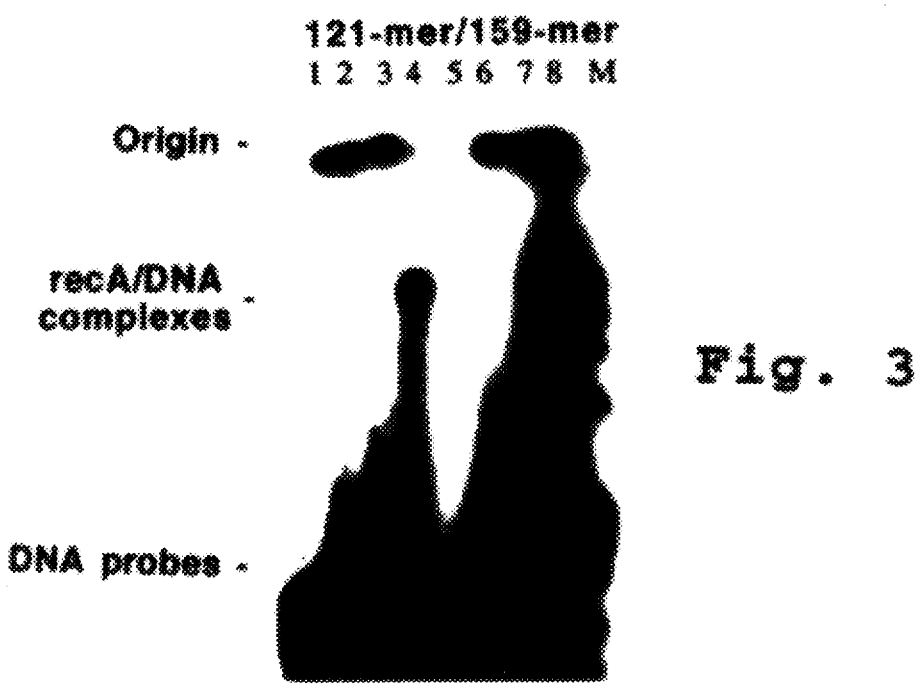
FIG. 3 shows an autoradiogram of a DNA band-shift gel electrophoresis assay to illustrate RecA protein binding to DNA probes.

The coating of probes with RecA protein can be evaluated in a number of ways. First, protein binding to DNA can be examined using band-shift gel assays (McEntee et al.). Example 3 describes the use of the DNA band-shift gel assay to illustrate RecA protein binding to DNA probes. Labelled probes were coated with RecA protein in the presence of ATPγS and the products of the coating reactions were separated by agarose gel electrophoresis: FIG. 3 shows an autoradiogram of the resulting DNA in the gel. The data presented in FIG. 3 illustrates that following incubation of RecA protein with denatured duplex probe DNAs the RecA protein effectively coats single-stranded DNA probes derived from denaturing the duplex probe. As the ratio of RecA protein monomers to nucleotides in the probe increases from 0, 1:27, 1:2.7 to 3.7:1 for 121-mer (lanes 1-4, respectively) and 0, 1:22, 1:2.2 to 4.5:1 for 159-mer (lanes 5-8, respectively), DNA probe's electrophoretic mobility decreases, i.e., is retarded, due to RecA-binding to the DNA probe. The partial retardation of the DNA's probe mobility observed in lanes 2,3 and 6,7 reflects the non-saturation of probe DNA with RecA protein. Thus, as expected (Leahy et al.), an excess of RecA monomers to DNA nucleotides is required for efficient RecA coating of short DNA probes.

A second method for evaluating protein binding to DNA is the use of nitrocellulose filter binding assays (Leahy et al.; Woodbury et al.). The nitrocellulose filter binding method is particularly useful in determining the dissociation-rates for protein:DNA complexes using labeled DNA. In the filter binding assay, DNA:protein complexes are retained on a filter while free DNA passes through the filter. This assay method is more quantitative for dissociation-rate determinations because the separation of DNA:protein complexes from free probe is very rapid.

Typically, to perform such filter binding assays nitrocellulose disks (Schleicher and Schuell, BA85 filters or HAW POO25 nitrocellulose filters) are pretreated, soaked in buffer and then placed on a vacuum filter apparatus DNA:protein binding reactions are often diluted to reduce the concentration of components without dissociating complexes. The reactions are passed through the discs with vacuum applied. Under low salt conditions the DNA:protein complex sticks to the filter while free DNA passes through. The discs are placed in scintillation counting fluid (New England Nuclear, National Diagnostics, Inc.), and the cpm determined using a scintillation counter.

C. DNA Targets.

To study the specificity of the RecA catalyzed hybridization of probes with homologous double-stranded linear DNA targets at internal sites, several model lambda DNA target systems were used including the following:

(1) A mixture of 14 DNA fragments, ranging in size from 92 to 8598 bp generated by DraI (Promega) restriction enzyme digestion of complete lambda genomic DNA (48.5 kb; Bethesda Research Laboratories, Gaithersburg Md.). The target fragment homologous to the region defined in FIG. 1 and 2 is a 8370 bp DraI fragment. The region(s) of homology to the probes, listed in Table 1, were all at least 832 bases in from the 3' end of the double-stranded target DNA fragment.

(2) A mixture of two fragments (38,412 and 10,090 bp) generated by ApaI restriction enzyme digestion of complete lambda genomic DNA. The approximately 10 kb fragment contains the region defined in FIGS. 1 and 2. This region of homology lies at least 2460 bp from the 3' end of the double-stranded target DNA fragment.

(3) The 10 kb fragment of an ApaI lambda DNA digest, agarose gel purified and deproteinized.

(4) A double digest of lambda with DraI and BamHI in which the target DNA fragment is 2957 bp, with probe target homology at least 832 bases from the 3' end of the double-stranded target DNA fragment.

(5) Whole lambda viral DNA was also used as target. In this case, probe:target homology was at least 7131 bases from the 5' end of the whole lambda genome.

D. RecA-Facilitated Formation of Hybridization Complexes Between Double-stranded Probe and Target DNA Sequences.

The mixing of RecA coated single-stranded DNA probes and target DNA initiates the search for homology between RecA coated DNA probes and duplex target DNA molecules. In the case of a single probe sequence, once the RecA:DNA probe filament is formed it can catalyze the search for homology and D-loop formation between complementary probe and target DNA sequences. Traditional single D-loops can be formed between single-stranded RecA-coated DNA probes with about 500 bases or less of homology with linear double-stranded target DNAs. These D-loops are unstable after protein removal when the position of probe:target homology is at an internal position on the linear target.

Experiments performed in support of the present invention have demonstrated that 500-mer and smaller probes can form stable deproteinized RecA catalyzed double D-loop probe:target complexes at internal sites on duplex linear DNA targets. However, to form such stable structures, at least two probes must be used that have overlapping complementary sequences to each other. The two probes are RecA coated single-stranded DNA probes and are used in RecA catalyzed probe:target hybridization reactions.

Figure 4A:
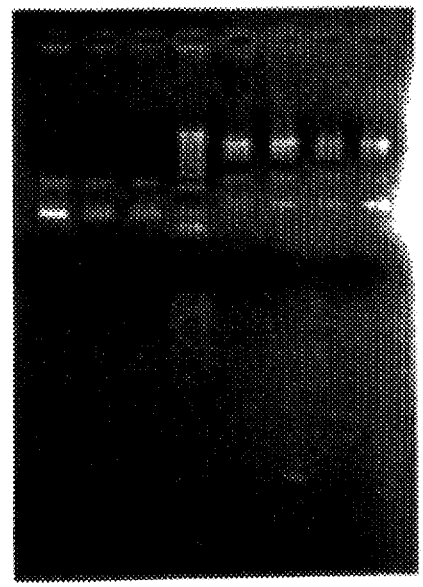
FIG. 4A shows an ethidium bromide stained gel on which the components of deproteinized hybridization reactions using 500-mer and 280-mer probes were resolved.

Example 4 describes the formation of RecA protein-mediated double D-loops, or multiplexes. The 500- and 280-mer probes were RecA protein-coated and the target DNA was the 8369 bp lambda DNA DraI fragment described above. The RecA protein to probe-nucleotide ratio was 1.5:1 for 500-mer and 1.3:1 for 280-mer. The double-stranded DNA probe to homologous double-stranded DNA target fragment ratio was 11:1 for 500-mer and 22:1 for 280-mer. FIG. 4A shows an ethidium bromide stained DNA gel on which the DNA components of the deproteinized hybridization reactions were resolved.

Figure 4B:
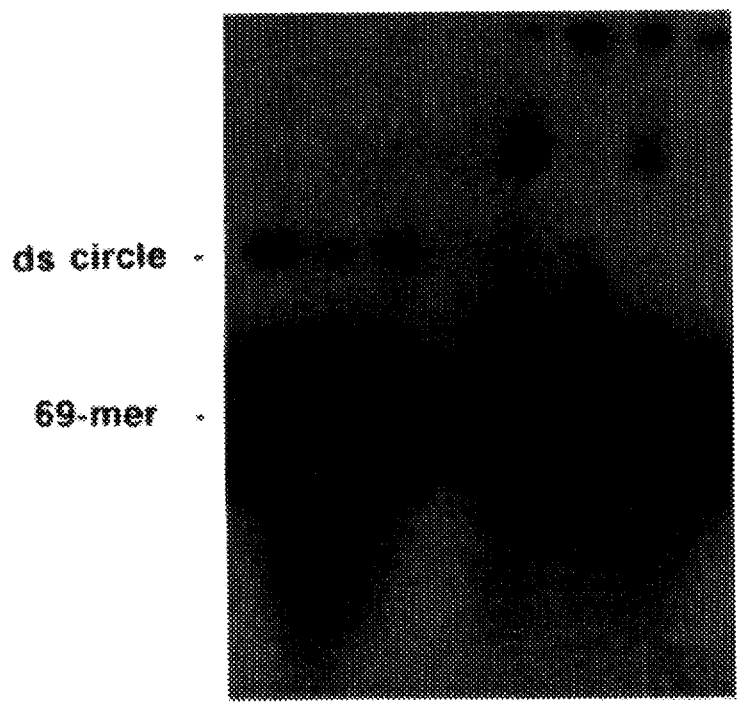
FIG. 4B shows an autoradiograph of the gel shown in FIG. 4A.

FIG. 4B shows an autoradiograph of the DNA in the gel shown in FIG. 4A. The results presented in FIG. 4B show formation of 500-mer:target and 280-mer:target DNA hybridization products that are stable to deproteinization. A comparison between the reactions with and without RecA protein, shows that RecA is required for the formation of homologous probe:target DNA complexes.

The pUC18 double-stranded circular DNA was included as a positive control in Example 4. Negatively supercoiled double-stranded DNA circular molecules are known to form probe:target RecA protein catalyzed hybridization products with short single-stranded probes that are stable to deproteinization (Rigas et al.; and Cheng et al., 1988).

In order to confirm the identity of the hybridization products formed in the above experiment, RecA protein coated probes were reacted with target fragments derived from DraI/BamHI double digest of lambda genomic DNA. In this experiment, the homologous target fragment generated by the double digest was 2957 bp in length and the position of probe:target sequence homology was unchanged from the previous experiments (i.e., 832 bs from the 3' end of the homologous target fragment). The hybridization reactions were performed under identical conditions to those just described for the 8370 bp lambda DNA DraI target fragment.

Electrophoretic separation followed by autoradiographic analysis of these RecA protein catalyzed hybridization reactions showed that deproteinized probe:target DNA complexes now migrated to the position of the 2957 bp target fragment, confirming that the probe:target DNA hybridization reaction was indeed with specific homologous targets.

The RecA protein catalyzed probe:target reactions were carried out in the presence of an excess of non-homologous linear DNA target molecules.

Figure 5A:
FIG. 5A shows an ethidium bromide stained gel in which the components of deproteinized hybridization reactions using 280-mer, 121-mer, and 79-mer probes were resolved.

Example 5 describes the formation of complexes stable to deproteinization between small double-stranded probes and linear double-stranded target DNAs. In the hybridization reactions presented in Example 5, denatured probes were coated at a RecA protein to probe-nucleotide ratio of 1.8:1, 0, 5.7:1, 5.9:1, 2.6:1 and 11.8:1, lanes 1–6, respectively in FIGS. 5A and 5B. The double-stranded probe to double-stranded target fragment ratios were 4.8:1 (280-mer), 3.6:1 (121-mer), and 5.2:1 (79-mer). FIG. 5A shows DNA from an ethidium bromide stained gel on which the components of the deproteinized hybridization reactions were resolved.

Figure 5B:
FIG. 5B shows an autoradiograph of the gel shown in FIG. 5A.

FIG. 5B shows an autoradiograph of the gel shown in FIG. 5A. The results presented in FIG. 5B show that the stable deproteinized hybridization probe:target product can be formed with probes shorter than 280 bases in size. The addition of too much RecA protein appears to decrease the amount of stable product formed in the DNA hybridization reaction (compare lanes 4, 5 and 6). Because the 121-mer and 79-mer probes used in this experiment were derived from restriction enzyme digestion of $^{32}$P end-labeled 280-mer and 500-mer duplex probes, each DNA probe contained either the 5' strand or the 3' strand labeled, not both, as with the 280-mer: the 5' and 3' ends of molecules are identified with respect to whole lambda DNA. The signals observed in lanes 3–6 of FIG. 5B show that either the 5' or the 3' probe strand can take part in the probe:target reaction: this observation is consistent with the conclusion that both probe strands are involved in the formation of the probe:target DNA hybridization complex that is stable to deproteinization.

Numerous hybridization experiments following the basic protocol described in Example 4 and 5 have confirmed that the RecA protein catalyzed hybridization reaction can occur under a broad range of reaction conditions. Typically, when different concentrations of target DNA are used, the yield of deproteinized hybrid is proportional to the amount of homologous target DNA in the reaction. Some reactions conditions can be summarized as follows:

(i) ATPγS concentrations between 1 and 12 mM were tested in probe RecA-coating reactions. This concentration range of ATPγS gave stable hybridization products after target addition: the preferred range was about 2.4 to 8 mM. ATPγS, rATP (alone and in the presence of a regenerating system), dATP, GTPγS, and mixes of ATPγS and rATP, also work in probe coating reactions (Examples 10 and 11). Further, when commercial preparations of ATPγS are used in a reaction, the purity of the preparation can vary from preparation to preparation. ATPγS obtained from Pharmacia are usually approximately 95–97% ATPγS. ATPγS obtained from Sigma vary between approximately 75% to approximately 90% ATPγS: these preparations usually contain between approximately 10% to 20% ADP. ATPγS from both Pharmacia and Sigma sources have been tested: preparations from both of these sources work well in RecA double D-loop reactions. Thus, combinations of ATPγS and ADP also work in RecA mediated double-D-loop hybridization reactions. Further, DNA probes were effectively coated with RecA protein in the presence of a mixture of ATPγS and rATP, preferred mixtures contained about 1.4 and 1 mM of each component, respectively. The results of these experiments show that RecA can use a wide variety of cofactors and cofactor combinations for double D-loop complex formation.

(ii) Mg$^{++}$ acetate concentrations in the final reaction containing the probe and target DNAs worked overt a broad range of Mg$^{++}$ concentrations: 4 to 25 mM, with the preferred range being about 6 to 8 mM;

(iii) RecA protein concentrations between 8.4 to 41 µM were tested in probe coating reactions: each concentration was active;

(iv) RecA protein to probe-nucleotide ratios during probe coating between 1:3 and 6:1 were effective with the preferred range being between about 2:1 and 4:1 ratios;

(v) Final (micromolar) double-stranded DNA probe to double-stranded DNA target molecule ratios were between 2:1 and 22:1 all yielded stable deproteinized probe:target hybrids;

(vi) The DNA hybridization reaction works in an analogous Tris-HCl reaction buffer (pH 7.5), although probe coating and strand transfer in acetate buffer appears to give more products than the Tris system;

(vii) recA-803 mutant protein was active in forming stable hybridization complexes;

(viii) The hybridization reaction functions in the presence of single-strand binding (SSB) protein (Morrical et al.);

(ix) RecA protein coated single-stranded DNA probes, including mixtures of coated-denatured-double-stranded probes, stored at –20° C. for several days were active in hybridization complex formation after incubation with target at 37° C.;

(x) The hybridization reaction can be carried out with whole lambda genomic DNA as target. The probe:target hybridization reactions can be also be carried out when the target DNA is embedded in agarose plugs or microbeads: for example, stable double D-loop hybrids have been formed using RecA-protein coated probes with intact 48.5 kb λ DNA targets embedded within agarose plugs;

(xi) The region of complementary overlap between the probe strands typically is about 79 base pairs and less than about 500 base pairs. Probes with this degree of complementary overlap form stable products at internal target sites in the RecA-catalyzed hybridization reaction of the present invention. Generation of stable hybridization products was also demonstrated at the ends of linear molecules (for example, using 80-mer probes and the 500-mer duplex as target (FIG. 1)). Standard probe-strand to target-strand complementarity is between 90–100%. However, RecA protein is known to catalyze the formation of hybridization complexes containing some non-specific base pair interactions (Cheng et al. 1989). Accordingly, probe:target complementarity can be reduced depending on probe size and the required specificity of the detection reaction: typically complementarity is not lower than 70% base pair matches between each probe-strand and target-strand.

(xii) Probes having less than about 79 base pairs of overlap can be used in the present invention: stabilization of the double D-loop, subsequent to deproteinization, may be advantageous when probes of these smaller sizes are used. One method of further stabilizing the double D-loop complexes is psoralen cross-linking (Cheng et al., 1988): such cross-linking is particularly useful in situ since it permits the use of harsh washing conditions.

Figure 7:
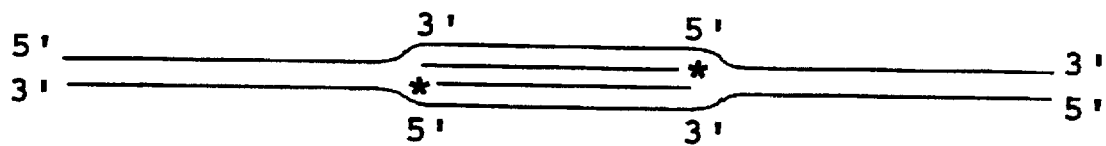
FIG. 7 illustrates a model of stable double-stranded probe:duplex linear target DNA complexes.

The results presented in FIG. 5B indicated that the observed probe:target products were stable to deproteinization because both DNA probe strands were present on the same target molecule. One representation of such a stable complex is shown in FIG. 7. This structure is referred to herein as a double D-loop or multiplex DNA structure as opposed to the traditional single D-loop, or triple-stranded displacement loop or triplex structure (two target strands and a single DNA probe complementary to a particular single target strand).

Example 6 presents data that confirms that two RecA protein-coated DNA probe strands are required for the production of stable deproteinized probe:target hybridization products on a linear target DNA molecule at an internal region of DNA homology. Individual 121-mer probe strands were chemically synthesized to insure that individual probe strands would not be contaminated with small amounts of the complementary (opposite) DNA strand. In order to distinguish the presence of each of the two individual complementary DNA probe strands, the probes were differentially labeled: one strand with a 5' terminal $^{32}$P label and the other with a single 5' terminal biotin label.

Figure 6A:
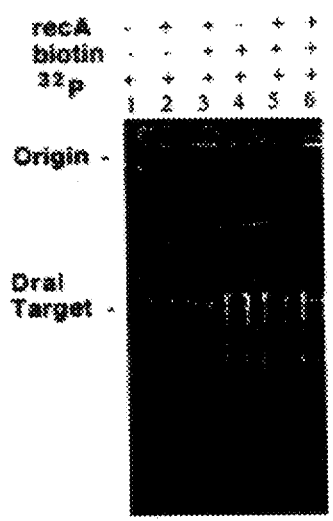
FIG. 6A shows an ethidium bromide stained gel in which the components of deproteinized hybridization reactions using differentially labeled 121-mer DNA probes were resolved.

Since only one strand was radioactively labeled the $^{32}$P specific activities of each double D-loop DNA hybridization reaction were the same: accordingly, comparison between the results of all experiments was more convenient. Hybridization reactions were performed as described in Example 6. FIG. 6A shows an ethidium bromide stained gel on which the DNA components of the deproteinized hybridization reactions were resolved.

Figure 6B:
FIG. 6B shows an autoradiograph of the gel shown in FIG. 6A.

FIG. 6B shows an autoradiograph of the DNA in the gel shown in FIG. 6A. The results in FIG. 6B show that two probe strands are required for stable deproteinized probe:target hybrid production. In addition, the reaction works whether both probes are coated with RecA protein together or in separate reactions. Further, the hybridization reaction generates deproteinized stable complexes even when the DNA probes are added to the reaction sequentially (lanes 5 and 6). The addition of the $^{32}$P strand first to the reaction mix appears to provide more DNA hybridization product. It is possible that the terminal biotin label is slightly inhibitory due to the size of the chemical spacer arm or the position of the label on the probe. However, regardless of the order of probe addition to the hybridization reactions, two probe strands are required to generate stable deproteinized homologous complexes. The RecA-mediated homologous probe targeting reaction can also use probes containing biotin incorporated at internal positions. Such probes can be synthesized using a modification of polymerase chain reaction (Mullis; Mullis, et al.) where bio-14-dATP replaces a certain percentage (e.g., 5 to 25%) of the dATP normally used during synthesis.

The rate of RecA-facilitated homologous pairing of short DNA probes to their cognate target sequences has been shown to be positively related to the length of attached heterologous DNA tails (Gonda et al.). Accordingly, probes used in the hybridization reactions of the present invention may include heterologous tails, i.e., terminal sequences that are non-homologous to the target DNA, in order to speed the homologous pairing of the probe sequence to the target sequence.

E. Capture/Detection System.

Figure 8:
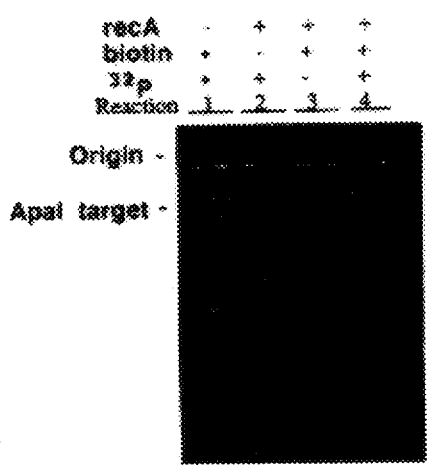
FIG. 8 shows a gel from which stable double-stranded probe:duplex linear target DNA complexes were isolated, where the duplex probe strands were differentially labeled.

The presence of both the $^{32}$P- and biotin-labeled 121-mer probe strands on the same target molecule was further confirmed using a capture/detection system (Example 7). The deproteinized double D-loop products were captured using streptavidin-magnetic beads. Capture of the biotin containing probe simultaneously captured the $^{32}$P-labelled probe. FIG. 8 shows the DNA from the gel from which the probe:target complexes were isolated before streptavidin capture of the biotin moiety. The DNA complexes were isolated by extraction from gel fragments corresponding to the expected size of the probe:target complex (Example 7). The extracted DNA was then exposed to streptavidin-coated paramagnetic beads. The beads were then isolated and placed in scintillation fluid for detection of the $^{32}$P-labelled DNA probe strand. The results of this analysis are presented in Table 2. The data show that only reactions using two probe strands and RecA protein give a capture signal above background. This experiment used isolated DNA target migrating at the 10 kb target DNA position for capture, thus ruling out the possible presence of complex recombination products between multiple 10 kb targets that could be captured and detected without actually having a double D-loop structure on an individual 10 kb target molecule. Further, the hybrid molecules formed in these reactions are quite stable under the isolation conditions used supporting the conclusion that the captured $^{32}$P signal was not an artifact of complementary probe reassociation.

II. Utility

FIG. 9 shows a number of possible double D-loop structures. FIG. 9A represents the formation of a double D-loop structure at an internal site on a DNA target molecule. FIG. 9B represents a similar structure except that the probe DNA molecules have been tailed with heterologous DNA (Gonda et al.). Such tailing can serve several purposes: (i) facilitating RecA loading onto small probes; (ii) providing an extension molecule for the inclusion of labels in the probe, for example, digoxigenin or biotin; (iii) providing a capture sequence; and (iv) providing a sequence to hybridize to an additional reporter molecule.

Figure 9A:
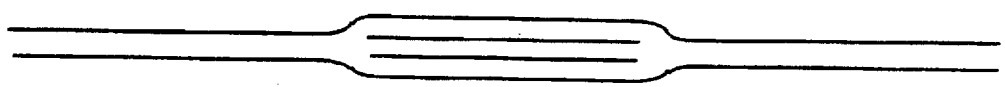
FIG. 9 illustrates a variety of double-stranded probe:duplex linear target DNA complexes.
Figure 9B:
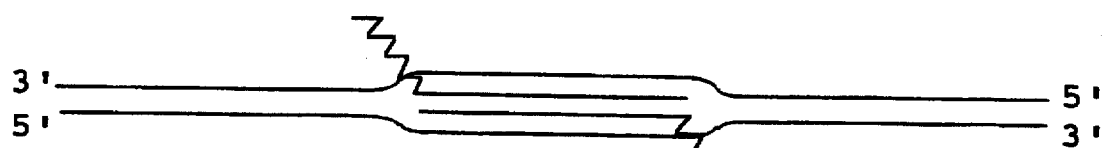
Figure 9C:
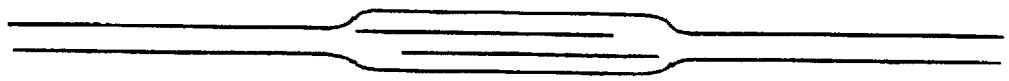

FIG. 9C represents the situation where two probes are used that have a region of complementary overlap (i.e., a region in which they are complementary to each other) in addition to homologous terminal extensions (i.e., regions complementary to the target DNA but not to the other probe).

Figure 9D:
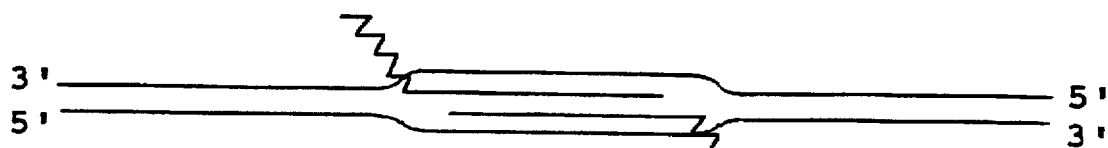
Figure 9E:
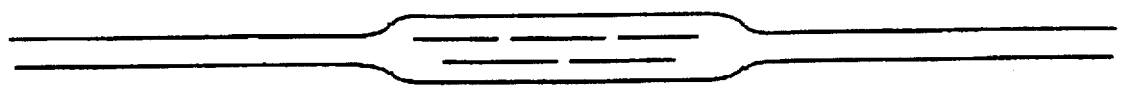
Figure 9F:
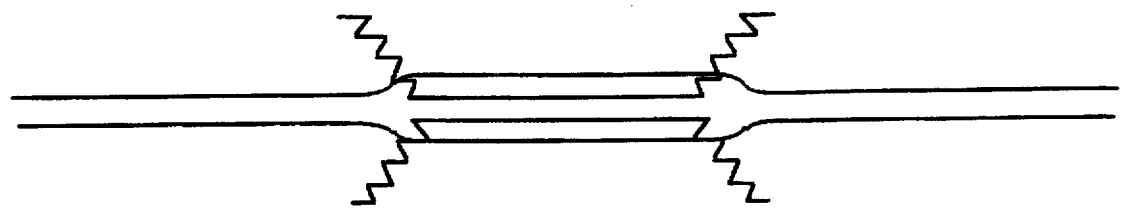
Figure 9G:
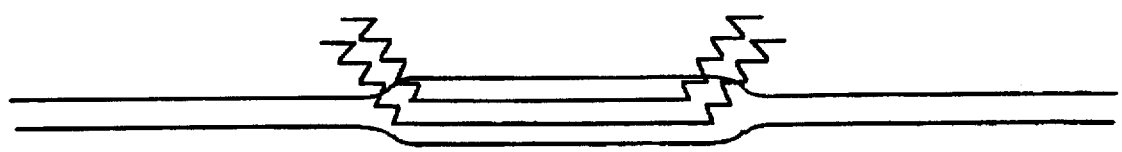

FIG. 9D represents the situation where two probes are used that have a region of complementary overlap in addition to heterologous terminal extensions (i.e., regions not complementary to the target DNA but not to the other probe). FIG. 9F shows a similar situation where heterologous terminal extensions are present at both the 5' and 3' ends of each probe strand. FIG. 9G illustrates the situation where the homologous tails are complementary to each other, but not to the target DNA.

The double D-loop structures need not be composed of only two probes. For example, FIG. 9E shows a double D-loop structure generated from 5 separate probe strands: the internal probe strands have regions of complementary overlap to more than one other probe strand. The total region of complementary overlap is typically 79 to 500 base pairs, but, as discussed above, this region may be smaller.

The structures in FIG. 9 illustrate several, but not all, possible combinations of probe and target DNA that can generate double D-loop structures stable to deproteinization. One common feature of double-stranded probes to be used in double D-loop reactions is a region of complementary overlap between the probe strands.

The ability to form stable RecA protein catalyzed deproteinized double D-loop probe:target complexes at internal sites allows specific identification of homologous linear DNA targets. This double D-loop reaction provides new possibilities for hybridization diagnostics. The assay provides the advantages that differentially labeled complementary probe strands can be used in a single reaction and only one small target sequence needs to be known.

Reassociation of complementary probes is inhibited when saturating levels of RecA protein are used (Bryant et al.). Reassociation of such probes is also reduced by the inclusion of ATPγS as a cofactor in the probe coating reactions.

As described above, the complexes of the present invention, which are formed between the RecA protein coated probes and target DNAs, are stable to deproteinization reactions (as described). In some applications, however, the removal of RecA protein from the complexes is not required for practicing the application. In such cases the only limitation is that the remaining protein molecules do not interfere with the application (e.g., see Section F below).

A. Target DNAs.

The method of the present invention can be used to diagnose infectious disease caused by organisms in clinical samples. These organisms can be diagnosed by the detection of specific DNA characteristic of the causative organism. Such organisms include the following: bacteria, like Salmonella, Neisseria, Chlamydia, Shigella, and Streptomyces; viruses, like Herpes simplex virus-1 (HSV-1), herpes simplex virus-2 (HSV-2), and adenovirus, all double-stranded DNA viruses; parasites, like Plasmodium and Giardia; and mycoplasma, like *Mycoplasma pneumonia, M. genitalium* and Pneumocystis.

For any diagnostic assay, probe sequences are chosen to a known region of homology in the target DNA. Target DNA can be prepared from a number of different sources by standard techniques: for example, aqueous solutions, mammalian tissue, cultured cells, plant tissue, bacteria, yeast, blood and blood components (Ausubel et al.; Maniatis et al.; Sambrook et al.; Davis et al.; Fey; Strickler et al.; Kingston; Wachsmuth).

In general, the detection methods of the present invention can be applied to the detection of duplex DNA in any nucleic acid sample. Applications other than clinical diagnosis of infectious diseases include (i) screening cultured mammalian cells for the presence of contaminants, such as mycoplasma (Zlvin et al.), (ii) diagnosis of certain genetic diseases caused by specific deletions/mutations, insertions or rearrangements in mammalian DNA, such as α-thalassemia, β-thalassemia, or chronic myelocytic leukemia and (iii) hybridization probes to distinguish the presence or absence of a given target sequence in a duplex DNA molecule.

B. The Use of One Double D-loop Structure for Diagnostic Applications.

FIG. 10 illustrates several embodiments of the use of one double D-loop structure for the isolation and identification of corresponding sequences in duplex DNA targets. One probe can be labeled with a capture moiety (e.g., as was done with biotin in Example 7). The other probe is then labeled with a detection moiety, such as a radioactive label, biotin, or digoxigenin or other modified bases. The probes are coated and hybridized to the nucleic acid sample that is being tested for the presence of the target sequence. The hybridization reactions can be deproteinized or used directly.

The probe labeled with the capture moiety is trapped. This trapping can be accomplished by, for example, labeling the probe with a biotin moiety and exposing the reaction mixture to streptavidin that has been attached to a solid support. Alternatively, the capture moiety can be digoxigenin and the trapping can be accomplished using an antidigoxigenin antibody attached to a solid support. Additional groups can be conveniently attached to the ends of DNA molecules as follows. The oligonucleotide probe is combined with digoxigenin-11-dUTP (an analog of dTTP, 2'-deoxy-uridine-5'-triphosphate, coupled to digoxigenin via an 11-atom spacer arm, Boehringer Mannheim, Indianapolis IN) and terminal deoxynucleotidyl transferase (GIBCO BRL, Gaithersburg, Md). The number of dig-11-dUTP moieties incorporated using this method appeared to be less than 5 (probably only 1 or 2). Alternatively, dig-11-dUTP moieties can be incorporated into the oligonucleotide sequence of a probe as with biotin.

Typically, the following combinations of double-stranded probes are used in the capture detection system: (i) first probe/capture, labeled with biotin or digoxigenin, second probe/detection, radiolabeled; (ii) first probe/capture, labeled with biotin, second probe/detection, labeled with digoxigenin; or (iii) first probe/capture, labeled with digoxigenin, second probe/detection, labeled with biotin.

One convenient method to sequester captured DNA is the use of streptavidin-conjugated superparamagnetic polystyrene beads as described in Example 7. After capture of DNA, the beads can be retrieved by placing the reaction tubes in a magnetic rack.

Alternatively, avidin-coated agarose beads can be used. Biotinylated agarose beads (immobilized D-biotin, Pierce) are bound to avidin. Avidin, like streptavidin, has four binding sites for biotin. One of these binding sites is used to bind the avidin to the biotin that is coupled to the agarose beads via a 16 atom spacer arm: the other biotin binding sites remain available. The beads are mixed with hybridization complexes to capture biotinylated DNA (Example 7). Alternative methods (Harlow et al.) to the bead capture methods just described include the following streptavidinylated or avidinylated supports: low-protein binding filters, or 96-well plates, or modified biotin capture methods such as iminobiotin (Rigas, B., et al.).

For either of the above bead methods, the beads are isolated and the amount of hybridization complex that has been captured is quantitated. The method of quantitation depends on how the second strand DNA probe has been prepared. If the second probe is radioactively labelled the beads can be counted in a scintillation counter. Alternatively, the captured DNA may be detected using a chemiluminescent, fluorescent or colorimetric detection system.

Many of the experiments described above have made use of radio-labelled oligonucleotides: Example 7 combines the use of a biotin labeled first probe with a radioactively labelled second probe. The techniques involved in radiolabeling of oligonucleotides have been discussed above. A specific activity of $10^8$ cpm per µg DNA is routinely achieved using standard methods (e.g., end-labeling the oligonucleotide with adenosine [$\gamma$-$^{32}$P]-5' triphosphate and T4 polynucleotide kinase). This level of specific activity allows small amounts of DNA to be measured either by autoradiography of gels or filters exposed to film or by direct counting of sample in scintillation fluid.

Radiolabeling and chemiluminescence (i) are very sensitive, allowing the detection of sub-femtomole quantities of oligonucleotide, and (ii) use well-established techniques. In the case of chemiluminescent detection, protocols have been devised to accommodate the requirements of a mass-screening assay. Non-isotopic DNA detection techniques have principally incorporated alkaline phosphatase as the detectable label given the ability of the enzyme to give a high turnover of substrate to product and the availability of substrates that yield chemiluminescent or colored products.

For chemiluminescent detection, biotinylated or digoxigenin-labelled oligonucleotide probes can be detected using the chemiluminescent detection system "SOUTHERN LIGHTS", developed by Tropix, Inc. The basic technique can be applicable to detect DNA that has been captured on either beads, filters, or in solution.

Alkaline phosphatase is coupled to the captured DNA complex. To do this several methods, derived from commonly used ELISA (Harlow et al.; Pierce, Rockford Ill.) techniques, can be employed. For example, the second strand DNA probe can be end-labelled with digoxigenin-11-dUTP (dig-11-dUTP) and terminal transferase (as described above). After the DNA is captured and removed from the hybridization mixture, an anti-digoxigenin-alkaline phosphatase conjugated antibody is then reacted (Boehringer Mannheim, Indianapolis Ind.) with the digoxigenin-containing oligonucleotide. The antigenic digoxigenin moiety is recognized by the antibody-enzyme conjugate.

Captured DNA hybridization products are detected using the alkaline phosphatase-conjugated antibodies to digoxigenin as follows. One chemiluminescent substrate for alkaline phosphatase is 3-(2'-spiroadamantane)-4-methoxy-4-(3'-phosphoryloxy) phenyl -1,2-dioxetane disodium salt (AMPPD). Dephosphorylation of AMPPD results in an unstable compound, which decomposes, releasing a prolonged, steady emission of light at 477 nm. Light measurement is very sensitive and can detect minute quantities of DNA (e.g., $10^2$–$10^3$ attomoles).

Colorimetric substrates for the alkaline phosphatase system have also been tested. While the colorimetric substrates are useable, use of the light emission system is more sensitive.

An alternative to the above biotin capture system is to use digoxigenin in place of biotin to modify the first strand probe: biotin is then used to replace the digoxigenin moieties in the above described detection system. In this arrangement the anti-digoxigenin antibody is used to capture the DNA hybridization complex. Streptavidin conjugated to alkaline phosphatase is then used to detect the presence of captured oligonucleotides.

Other alternative capture systems include the following: (i) the use of a DNA binding protein and its cognate binding sequence, where the cognate binding sequence is the capture moiety that is included as a 5' terminal sequence in the first strand probe-(Kemp et al.); and (ii) the use of hybridization capture where a non-target-complementary DNA sequence, such as poly(T), is incorporated as a 5' terminal sequence in the first strand probe, and a complementary nucleic acid, such as poly(A), is used to capture the probe and associated nucleic acid by hybridization. Either of these two methods can be used in conjunction with a solid support.

Another alternative system is to fix one probe to a membrane (Saiki et al.), coat the probe, add target and the second coated probe, deproteinize, wash and detect.

FIG. 10 illustrates several arrangements for one double D-loop structure detection. FIG. 10A shows one probe strand labeled with a capture moiety, such as biotin, and the second probe strand labeled with a detection moiety, such as digoxigenin. FIG. 10B shows one probe strand labeled with a capture moiety, such as digoxigenin, and the second probe strand having a homologous tail extension that is labeled with multiple detection moieties, such as biotin. FIG. 10C illustrates the addition of detection (or capture moieties) to heterologous tails attached to either and/or both strands of the double-stranded probe.

C. The Use of Multiple Double D-loop Structures for Diagnostic Applications.

In addition to exploiting one double D-loop structure complexes in capture/detection systems, multiple double D-loop structures can be used as well. In cases where reassociation of probe strands may be a problem, for example with larger probes, the use of multiple double D-loop structures provides for a reduced background. In this method two or more sequences need to be known in the target sequence.

FIG. 11 illustrates several arrangements for detection based on two double D-loop structures. FIG. 11A shows an example of labeling both strands of a first duplex probe with the capture moiety and both strands of a second duplex probe with a reporting/detection group. The capture moiety can be contained in either one or both strands of the first probe set. In this system the hybridization complexes are captured as described above, however, reassociation of the strands of the first duplex probe generates no background for the reaction since neither strand contains a reporter/detection group. After capture, the hybridization complexes are detected on the basis of the presence of the second duplex probe in the hybridization complex. Detection of the reporter group is accomplished as described above.

A second embodiment of this system, based on the presence of multiple double D-loop structures in the target complex, is illustrated in FIG. 11B. In this case only one strand of the first duplex probe is labeled with the capture moiety and only one strand of the second duplex probe is labeled with the reporter moiety.

As described above for one double D-loop structure detection, heterologous tails and sequences homologous to the target DNA can be added to the duplex probes.

D. The Use of Double D-loop Structures in RecA protein Facilitated DNA Amplification Reactions.

DNA amplification reactions have been described that predominantly rely on thermal denaturation (Mullis; Mullis et al.; Scharf et al.) for strand separation in preparation for continued amplification. Described below are two detection systems based on DNA amplification subsequent to the formation of single or multiple double D-loops.

(i) One amplification/detection method of the present invention utilizes multiple double D-loop structures to facilitate amplification without the need for thermal denaturation.

Experiments performed in support of the present invention have demonstrated that use of two pairs of complementary DNA primers, which are homologous to different regions of the double-stranded target, in the hybridization reactions of the present invention results in the formation of two double D-loops in the target DNA. These double D-loops flank and define a specific region of DNA on a native duplex target (FIG. 12A): DL801/2 and DL803/4 (Table 1) are examples of probes/primers that can participate in this reaction.

The resulting DNA target structure is recognizable by various DNA polymerases as a substrate for DNA synthesis. An example of one such amplification reaction is presented in Example 8. The substrate for the amplification reaction described in Example 8 is the lambda DNA genome. The primers define a target region of approximately 500 bp. Typically, the amplificationreactions contain DNA polymerase (e.g., the Klenow fragment), RecA protein coated primers, ATPγS (or rATP (alone and in the presence of a regenerating system), dATP, GTPγS, and mixes of ATPγS and rATP or ATPγS and ADP), the target substrate, necessary cofactors and all four dNTPs (including modified or labeled dNTPs). These reactions may also contain DNA helicase, topoisomerase, or other similar DNA unwinding agents and/or other DNA polymerases.

These reaction conditions favor extension of the primers at their 3' ends with subsequent primer elongation in the 5' to 3' direction. The 3' end extension of two or more of the four DNA primers in the structure by polymerase defines regions of DNA target amplification between DNA primers (see FIG. 13). DNA polymerase extension of the other two primers can also occur at their 3' ends, unless these are chemically or physically blocked to restrict DNA amplification to a defined region (Example 8).

DNA polymerases catalyzing 3' extension between primer pairs may displace primers on the same strand, or, alternatively, new synthesized product(s) could be ligated to the primer with DNA ligase, including thermoresistant or thermosensitive DNA ligases (Epicentre Technologies, Madison, Wis.). Replication can also be facilitated by adding appropriate DNA helicase, topoisomerase, single-strand binding proteins (SSB), gene 32 (or other similar) proteins, or RecBCD-encoded enzymes or other proteins, some of which have associated helicase activities. Any primers properly positioned by RecA protein could be used for replication initiation.

Typically, probes used in the two-double D-loop RecA protein catalyzed DNA amplification are approximately 60 to 80 bp in size. Probes larger or smaller can also be used as well, but reaction conditions may need to be modified, for example, inclusion of stabilizing peptides (e.g., SSB or gene 32 protein), drugs, antibodies, polyamines or cross-linking reagents.

Multiple primers of different sizes can also be used. Primers can also be homologous to the target DNA duplex along their entire length, or they can contain end or internal regions of partial non-homology, such as heterologous tails (see above). The only requirement for these primers is that the bases used for the 3' extension of the desired amplification product is available to prime DNA synthesis. As described above, primers can also contain modified phosphate backbones or bases such as biotin or digoxigenin or appended functions such as DNA modifying enzymes and chemical agents.

Reaction in the presence of excess RecA protein-coated primers allows formation of new multiple or double D-loops on the newly replicated and amplified DNA. The RecA protein-coated primers serve to initiate additional rounds of DNA synthesis, and in this way the DNA target is amplified without the need for thermally denaturing the target DNA to position the amplification primers.

DNA amplification reactions can use any of a number of DNA polymerases or polymerase mixtures, including the following: Klenow large fragment of *E. coli* DNA polymerase I; T7; T4; and/or other viral or cellular DNA polymerases and their mutants, for example, double-Klenow mutant proteins having no exonuclease activity.

The DNA products of two-double D-loop reactions are defined by the DNA primers used. The left and right primers to the double D-loop regions to be amplified define the 5' ends of the newly synthesized DNA amplification products. When the primers are not displaced, the newly synthesized DNA product can be ligated in a RecA-catalyzed amplification reaction as illustrated in FIG. 12B.

Using multiple primer sets, it is also possible to generate DNA amplification products which have cohesive ends. The DNA products can then hybridize through their overlapping cohesive ends and the length of these associated DNAs is subsequently extended (Haase et al.). Elongation of existing strands, displacement synthesis, and RecA-catalyzed base pairing in the overlap regions may increase the yield of large DNA targets. This can be important for RecA-catalyzed DNA amplification in cells in situ, which may, under certain conditions (Haase et al.), require large DNA products or appended groups for retention in situ.

The double D-loop reaction, or multiple double D-loops, can be stably formed in agarose for in situ amplification reactions. Typically, the agarose is of the low-melting temperature variety, although mixtures of different types of agarose are possible, and the concentration of agarose is about 0.4–1%. Under these conditions the agarose gel provides a restrictive medium that also allows retention of shorter DNA products: this is particularly useful in in situ reactions (see below).

The RecA-facilitated DNA amplification reaction can be carried out at 37° C. as well as at elevated temperatures that are below the thermal denaturation temperatures of target DNA duplex or primer:target hybrids, for example 50°–60°C. Use of elevated temperatures in these reactions expands the repertoire of enzymes available for primer extension and may allow longer tracts of DNA to be synthesized. The temperature of the amplification reaction will dictate the choice of reaction components: for example, wild-type *E. coli* RecA-protein coated probes are added to the target DNA at 37°–39° C., DNA synthesis is then accomplished at 50°–55° C. with *Thermus aquaticus* DNA polymerase, the temperature of the reaction is then lowered to 37°–39° C. and RecA-protein coated probes are added re-added. Alternatively, at high temperatures temperature-resistant RecA-like proteins could replace the wild type *E. coli* RecA protein (as discussed in co-pending, co-owned, U.S. application Ser. No. 07/520,321).

The two-double D-loop, or multiple double D-loop, reaction using RecA protein-catalyzed primer positioning for DNA amplification reactions has important diagnostic applications for DNA detection and amplification in solution diagnostics or in situ diagnostics.

Figure 13A:
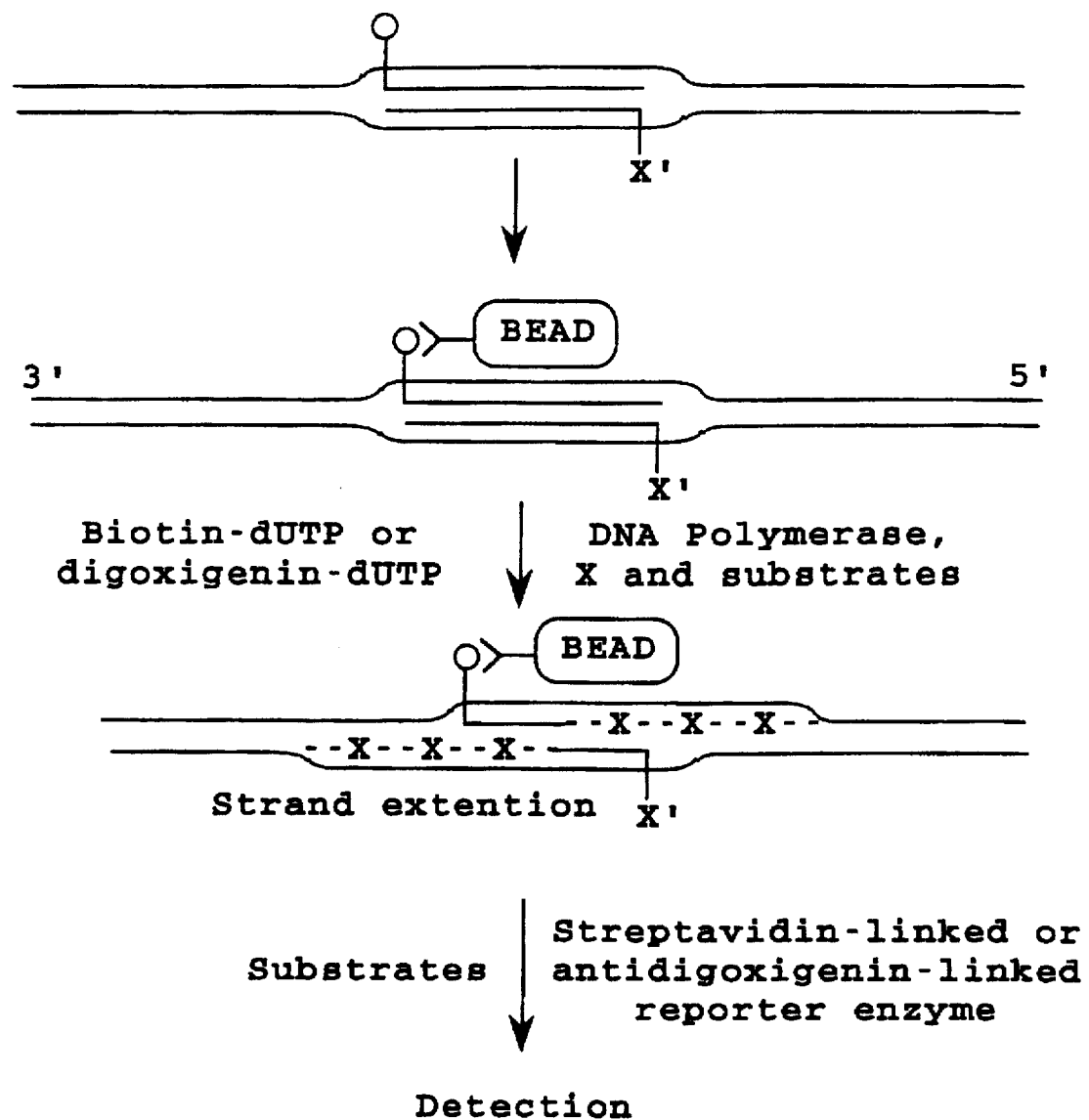
FIG. 13 shows a DNA polymerase mediated signal amplification reaction using a single double D-loop probe (FIG. 13A) or multiple double D-loop probes (FIG. 13B).

(ii) A second detection method exploiting the double D-loop and DNA amplification uses polymerase addition of labeled or modified dNTPs for signal amplification. Extension of the 3' end of a primer in a single (triple-stranded) D-loop structure using DNA polymerase was demonstrated by Cheng et al. (1988). After formation of a single double D-loop in a target DNA molecule DNA polymerase, necessary cofactors, and all four dNTPs are added to the reaction. Strand extension takes place from the 3' ends of either one or both probe strands of the double-stranded probe (FIG. 13A). Alternatively, the 3' end of the strand containing the capture moiety can be blocked to prevent primer extension. One or more of the dNTPs is labeled for detection by a standard method (e.g., biotin, digoxigenin, or, fluorescent or radioactive moieties). The incorporation of the labeled dNTP results in the amplification of the detection signal.

Figure 13B:
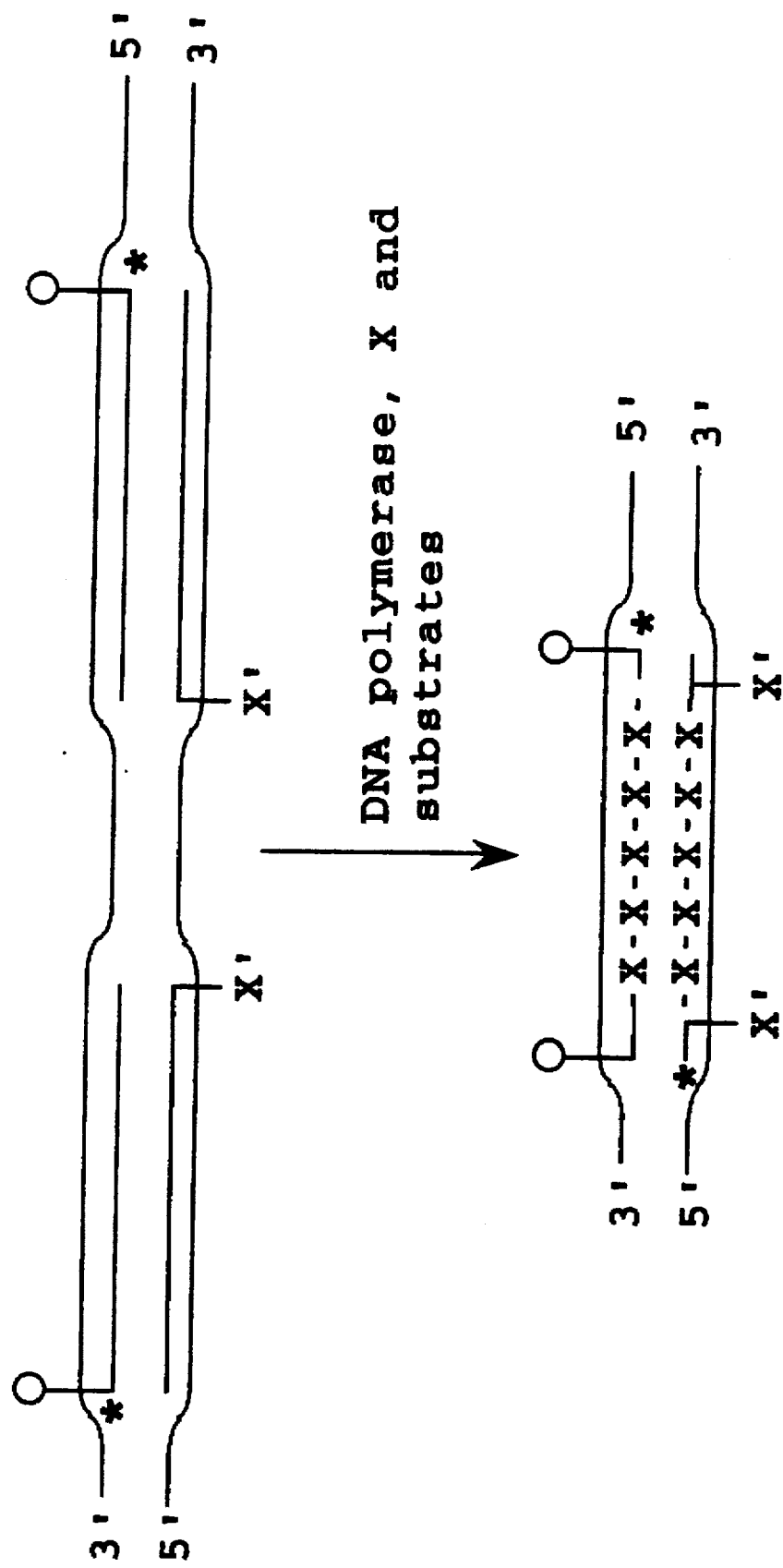

This method can be further exploited by using multiple double D-loop structures to target the region of interest (as described above). The 3'-ends of the double-stranded primers external to the target region can either be blocked (as illustrated in FIG. 13B by an asterisk) or not. This method of signal amplification can be further enhanced by using multiple rounds of RecA-facilitated amplification, as described above, in the presence of a labeled moiety.

Target detection with signal amplification can also be accomplished as follows. A double-D-loop is formed at the target sequence using two probe strands, where at least one of the strands contains a capture moiety. The resulting double-D-loop complex can be deproteinized and captured via contacting the capture moiety with a capture medium. The captured complex is released by heating: the complex can be released either as dsDNA or ssDNA. if necessary, e.g., if the complex is released as dsDNA, the complex is denatured and the target DNA released. To this mixture DNA synthesis primer(s), which are complementary to a target sequence, are added. These primers do not contain sequences that were present in the original double-stranded probe. DNA polymerase and dNTPs, are then added, under the appropriate buffer conditions, to synthesize DNA from the hybridized primer(s). This primer-directed template synthesis can be carried out in the presence of labeled dNTPs, for example, radiolabeled dNTPs, biotin-labeled dNTPs, FITC-labeled dNTPs, or other suitably labeled DNA precursors. The inclusion of label allows target detection via the appropriate detection systems, such as, a fluorometer in the case of FITC-label ed dNTPs.

E. The Use of Double D-loom Structures in RecA Protein Facilitated in situ Hybridization.

Another detection method which utilizes the double D-loop structure is in situ hybridization with fixed cells (Example 9): RecA-facilitated in situ hybridization methods have been described in co-owned PCT International Publication NO. WO 93/05177 "In situ Hybridization Method," published on Mar. 18, 1993. The in situ hybridization of RecA protein coated duplex probes provides the ability to localize a target sequence in an isolated, fixed biological structure or within a nucleus or nuclear volume relative to other targeted sequences and/or the nuclear membrane, using a confocal laser scanning microscope (van Dekken et al.).

One application of the in situ method is described in Example 9D. In this method, dividing HEp-2 nuclei are fixed and probed with the ReCA/chromosome-X alpha satellite DNA probe complex, and labeled with FITC-avidin. The pattern of probe bining in the dividing nucleus is evaluated using standard light fluorescent or laser scanning microscopic techniques. To localize the bound probe, the same field is viewed by phase contrast microscopy, without changing the focus of the lens. By overlaying the resulting two photomicrographs, the relative position of the nuclear membrane and nuclear division plane can be seen with respect to the probe-labeled chromosomes.

This aspect of the present invention provides simplified in situ procedures for localizing target sequence(s) in a biological structure. Typically, fixed cells or subcellular structures are probed in suspension or on slides followed by flow-cytometric or microscopic analysis. The method reduces artifaces by eliminating the need for a heat denaturation step, and allows more rapid and specific detection of target sequences. The method can be applied equally well to unique, low and/or high-copy number target sequences.

In particular, the method allows detection of low-copy sequences without the requirement to first amplify the sequences. Since most gene mapping and chromosomal studies are expected to involve specific, unique, or low-copy sequences, the present in situ method provides an important advantage for gene mapping studies, as well as for diagnostic applications involving unique or low-copy numbers of normal, mutant or pathogen sequences. Also, the present method allows for determination of chromosome content by flow cytometric analysis.

One general diagnostic application of this in situ method is for use in mapping a selected gene or regulatory sequence in a chromosome, and/or in a particular region of the chromosome. The target gene may be one which (a) generates a selected gene product, (b) is suspected of performing a critical cell-control function, such as a cell or viral oncogene, (c) is related to a repeat sequence, (d) is suspected of containing a genetic defect which prevents expression of an active gene product, (e) may be related in chromosome position to a marker probe region with a known map position, and/or (f) may represent an integrated viral sequence.

The probe strands for in situ hybridization can be labeled in a number of ways including direct labeling with fluorescent moieties like fluorescein-11-dUTP (Boehringer-Mannheim). Further, individual probe strands can be used to generate a coupled-fluorescence system where, for example, the emission energy of one fluorescent moiety, incorporated in one strand) emits light at the excitation energy of the second fluorescent moiety, incorporated in the second probe strand. Such a coupled-fluorescence system takes advantage of the proximity of the probe strands in the double D-loop complex.

When the DNA probes are directed against specific cellular pathogens, typically for detecting the presence of a viral or bacterial pathogen in an infected cell, the fixed labeled cells may be examined by light or fluorescence microscopy to detect and localize infecting pathogens in cells. Alternatively, cell infection, and percent cells infected, can be determined by fluorescence activated cell sorting (FACS) after in situ hybridization of RecA protein coated duplex probes to nuclei or cells in suspension (Trask et al.).

F. The Use of Double D-loop Structures in Restriction Enzyme Cleavage Based Detection Systems.

The double D-loop structures of the present invention can be used to detect the presence of target DNA in a sample by introducing alterations at the target/double D-loop complex which modify, in a detectable manner, the response of this complex to restriction enzyme digestion. Several examples of such detection systems are described below.

Figure 14:
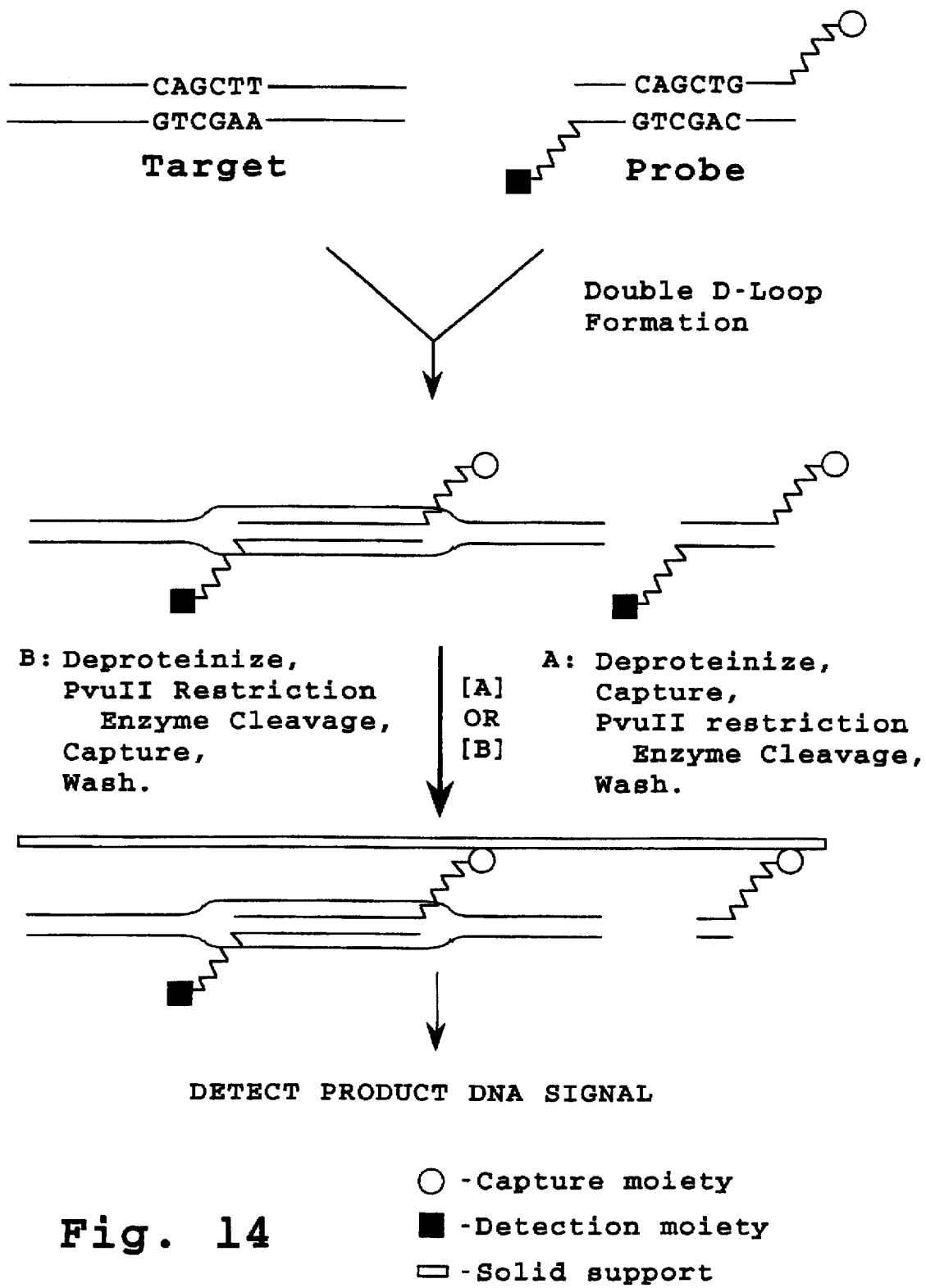
FIG. 14 illustrates a detection system involving the use of restriction endonuclease cleavage of non-target complexed double-stranded probe where capture of the resulting product is accomplished before (FIG. 14B) or after (FIG. 14A) restriction enzyme digestion.

One method of detection that exploits the double D-loop and restriction enzyme digestion is as follows. A region in the target DNA is chosen as the double-stranded probe sequence. The probe sequence is modified to contain an internal restriction site that is not present in the target DNA. Such a restriction site can be chosen so as to minimize base pair mismatching between the target and the probe (FIG. 14). The double D-loop is then formed and the complexes deproteinized. The complexes are then captured on the solid support and digested with the restriction enzyme for which the site has been introduced in the probe sequence (in FIG. 14A, PvuIII). Alternatively, the complexes can be digested with the restriction endonuclease before capture (FIG. 14B). Since the PvuII restriction site is not reconstituted when the probe is hybridized to the target sequence, the restriction enzyme will only cleave renatured probe:probe complexes, not probe:target complexes. The solid support is washed and examined for the presence of the detection moiety. This method allows the reduction of any background signal that may be generated by probe renaturation.

A second detection method works on a similar principle. In this method the target DNA is un-methylated and the double-stranded probe DNA is methylated before RecA protein-coating. The double D-loop complex is formed, the complex captured and deproteinized. The sample is then digested with, for example, DpnI which cleaves its recognition site (SEQ ID NO:2) only when the A residue on both strands is methylated. Since the methylated restriction site is not formed when the probe hybridizes to the target sequence, DpnI cleavage only occurs when the probes are renatured. The solid support is washed and examined for the presence of the detection moiety. As above, this method also allows the reduction of any background signal generated by probe renaturation.

The methylation state of the DNA can also be exploited using the target/double D-loop complexes as follows. In this method either the target DNA is methlated or the double-stranded probe is methylated prior to RecA protein-coating. The double D-loop complex is formed, the complex captured and deproteinized. The captured complexes can be isolated from the solid support and split into multiple samples. One sample is digested with a methylase-sensitive or methylase-dependent restriction enzyme and another is digested with a methylase-insensitive restriction enzyme: for example, MboI does not cleave DNA when the A residue is methylated and Sau3A I cleaves the same restriction site independent of the A residue's methylation state.

These samples can then be size fractionated (e.g., on an agarose acrylamide gel, or by HPLC) and the banding pattern of the samples compared. This method allows isolation and subsequent examination of restriction fragment length polymorphisms of a chosen fragment between a number of samples from different sources.

Figure 15:
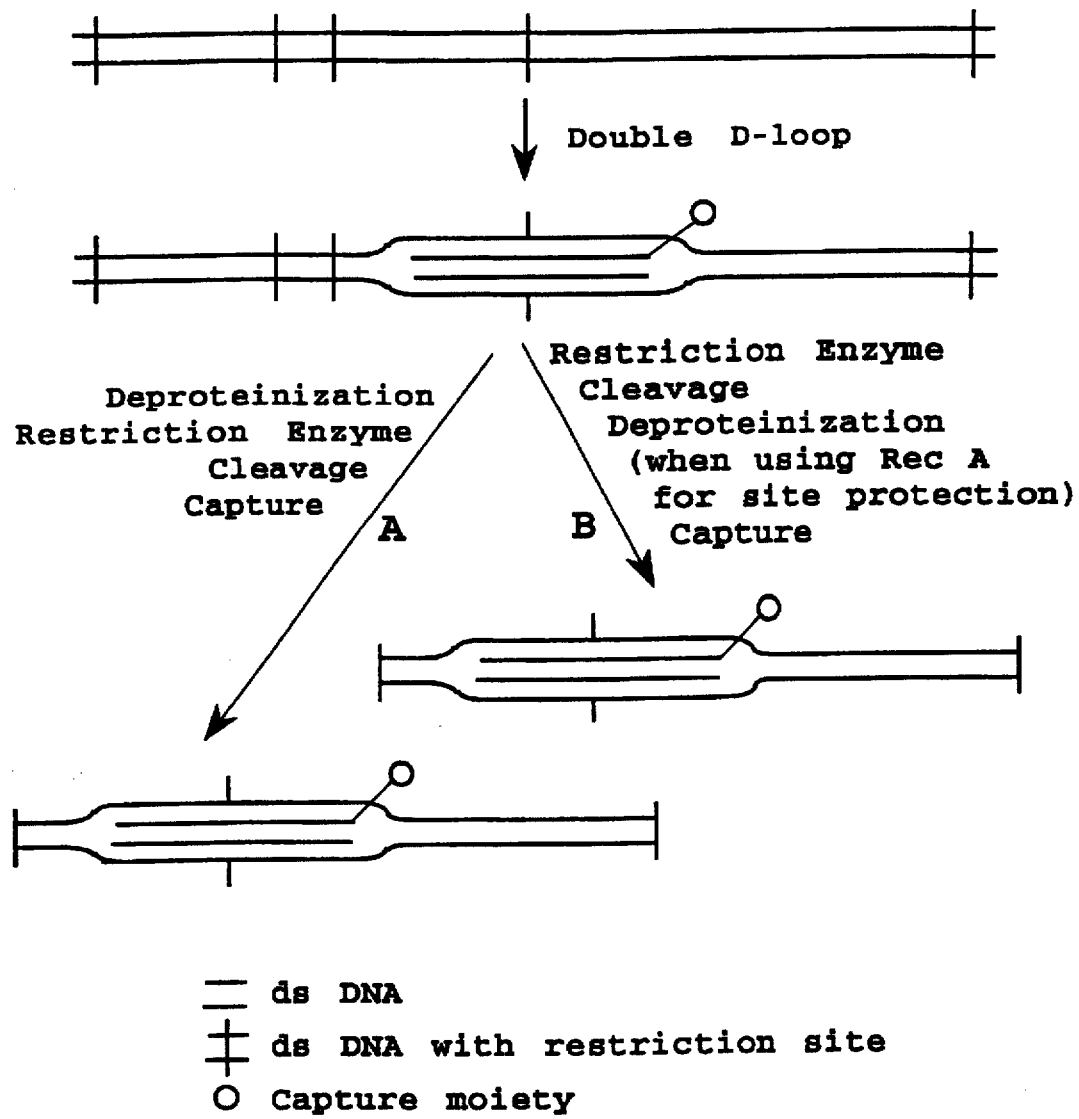
FIG. 15 illustrates the protection of a restriction site by either methylation or RecA protein. In the case of methylation protection the double D-loop complex is deproteinized before restriction endonuclease digestion (FIG. 15A). In the case of RecA protein protection the double D-loop complex is deproteinized after restriction endonuclease digestion (FIG. 15B).

Methylation may also be used to protect a specific restriction enzyme site from digestion (Nelson et al.). If, for example, it was desirable to isolate a MboI fragment spanning a particular region, but internal to the region an MboI site existed, the fragment could be isolated as follows. A double D-loop structure is formed at the internal restriction site in the target DNA using methylated probes. The target/double D-loop complex is deproteinized, digested with MboI and captured (FIG. 15A). This method can be used to (i) examine restriction enzyme polymorphisms at restriction sites adjacent to the protected site in fragments obtained from different sources, or (ii) capture and clone a desired sequence using a restriction enzyme even when an internal cleavage site is present for that enzyme. The fact that deproteinized double D-loop structures are susceptible to restriction enzyme cleavage has been demonstrated by PleI restriction endonuclease site-specific cleavage of probe:target complexes formed with 500-mer probes and 2.9-kb homologous target fragments.

The double-stranded RecA protein-coated probes can themselves be used to protect a specific restriction enzyme site from digestion. In this case, the complex is not deproteinized. The target/double D-loop complex is digested with the restriction endonuclease and captured (FIG. 15B). Alternatively, the double-stranded RecA protein-coated probes can be used to protect a modification site, for example, a methylation site, from modification. In this case, as for the above restriction site protection, the complex is not deproteinized. The target/double D-loop complex is treated with the modification reagent and then deproteinized. Modification target sites within the target/double D-loop complex are protected and lack the modification.

The ability to block restriction site cleavage is useful in genomic mapping. For example, if the target DNA defines a known region in the genome, like the PvuI site at approximately 26.3 kb on the lambda genome, the known site is protected by one of the approaches described above. Unprotected and protected lambda genomic DNA is digested with PvuI. The change in restriction fragment patterns between the two digests allows one to deduce which fragments are next to one another—based on the disappearance of bands and the sizes of the new bands in the sample containing blocked restriction sites.

Restriction enzymes, and their response to methylation states, are commonly available and conditions for their use are well known in the art (Ausubel et al.; Maniatis et al.).

G. The Use of Double D-loops to Generate Site-Specific Cleavage in DNA.

Oligonucleotides have been used to direct cutting agents to specific single-stranded and double-stranded nucleic acids sites (Corey et al.; Dreyer, G. B. et al; Moser, et al). One advantage of oligonucleotide directed cleavage is that the experimenter is no longer dependent on existing cleavage functions: any desired DNA cleavage function can be tailor-made. The RecA protein-coated double-stranded probes of the present invention can be used to generate site specific cleavage in a number of ways. For example, a specific target sequence is selected and a double-stranded DNA probe corresponding to the selected sequence is generated. An EDTA moiety is attached to one or both strands of the oligonucleotide probe. One method of attachment of EDTA to an oligodeoxynucleotide via the C-5 of thymidine has been described by Dreyer et al. The probe can then be RecA protein-coated and the double D-loop complex formed with target DNA. Cleavage occurs in the presence of oxygen upon addition of Fe(II) and a reducing agent (usually DTT) to the EDTA-probe:target hybrids.

Alternatively, cutting can be accomplished using peptide fragments derived from DNA binding/cleaving proteins (Sluka, J. P., et al.) which are attached to the oligonucleotide probes. Further, restriction endonucleases that have frequent cut sites or relatively non-specific phosphodiesterases, such as staphylococcal nuclease, can be attached to an oligonucleotide to generate a hybrid catalytic agent that has increased sequence specificity (Corey et al.).

Oligonucleotides are attached to the phosphodiesterase or other cleaving agent either before RecA protein-coating or after double D-loop complex formation and deproteinization. After association of the phosphodiesterase, nuclease or peptide with the double D-loop complex, the reaction conditions are modified to allow the hydrolysis of both target DNA strands in a site-specific fashion. Depending on the activity of the catalytic agent either one or both strands of the double-stranded probe is modified to contain the agent.

H. Use of the Double D-loop in DNA Enrichment.

The double D-loop hybridization complex of the present invention can also be used for separation and enrichment of selected target DNA sequences. For example, the double-stranded probe can be formed containing a capture moiety in one or both of the probe strands. The double D-loop complex is formed between the double-stranded probe and target DNA contained in a mixture of DNA. The double D-loop complexes that contain the probe and target sequence are then separated from the reaction mixture using the capture moiety, by, for example, attachment to a solid support. The complex can then be dissociated by heating to release the target duplex from the support and, if necessary, the released DNA renatured to regenerate the original target duplex DNA. Alternatively, the entire double D-loop complex may simply be released from the solid support.

To test whether the targeted duplex DNA could be released from the hybrids simply by heating, the thermal stability of deproteinized double D-loop hybrids formed with $^{32}$P-end-labeled 500-mer probes and the 10.1 kb ApaI target fragment was examined: the hybrids were completely stable at 75° C. in 1×TBE buffer. About half the DNA probe strands were released at 80° C. Essentially all of the DNA probe strands were released from the target at 85° C. This melting profile is similar to that for duplex probe:target hybrids formed by heating and then slowly cooling the reactant mixture in the absence of RecA protein. The hybrid melting profile was approximately 10° C. lower than that of duplex 500-mer probe, self-annealed, under identical ionic conditions.

The hybridization reaction is potentially useful for targeting chromosomal or gene fragments identified only by sequence-tagged sites (STSs) (Olson, et al.) for the following reasons:

(i) the RecA-mediated hybridization reaction does not require denaturation of the duplex DNA target for hybrid formation, and (ii) targets are released from isolated hybrids by heating to a temperature that dissociates the probe from the probe:target complex but that does not denature the duplex target-containing analyte, e.g., a chromosomal or gene-containing fragment. The target DNA analyte can then be recovered in duplex form.

Further, careful control of the hybrid melting temperature would permit a selection against the hybrids which might have only partial homology with the probe. Stringent melting temperature selection may be important when probes are used with complex mixtures of target DNAs. One advantage of recovery of duplex target DNA versus single-strand-denatured target DNA is that duplex DNA tends to be more resistant to shear forces than totally denatured single-stranded DNA. The recovery of duplex target DNA, by the method of the present invention, would allow the enrichment and isolation of specific duplex gene or genome segments, including large chromosomal fragments, which can then be used for further manipulations and/or analysis.

Target DNA duplexes obtained by this method can be used in DNA amplification reactions (Mullis; Mullis et al.) or in standard cloning techniques (Ausubel et al.; Maniatis et al.).

I. Homogeneous Diagnostic Assay

A protocol for a homogeneous diagnostic assay that can detect a specific native target DNA duplex has been tested. This assay involves double-stranded target capture using double D-loop hybrids followed by DNA signal amplification, as described briefly below.

(i) Capture of double-stranded DNA targets

A technique can be worked out for using double D-loop hybrids to specifically capture a large double-stranded DNA such as lambda DNA genome (~50 kb). The reaction is also applicable for the capture of smaller duplex DNA targets. The technique uses RecA-coated single-stranded probes labeled with a capture moiety such as biotin, preferably averaging 300–500 bases in size. All DNA probes are preferred to be homologous to sequences within preferably about 1000 base region of the duplex DNA target. The biotinylated probes are prepared by nick-translating preferably about 1000 bp DNA duplex fragment in the presence of bio-14-dATP. Heat-denatured probe DNA is coated with RecA protein and then reacted with duplex target DNA. After probe:target hybrid formation, the hybridization reaction mixture can be stopped, for example, with 20 mM EDTA and treated with 0.5M salt, and hybrids can be captured on washed magnetic Dynabeads® M-280 Streptavidin (Dynal). After capture, beads are washed 3× in buffer containing 1M salt. It is likely that the high salt conditions at least partially removed a proportion of the bound RecA protein. Target DNA capture can be measured by using $^{32}$P-labeled lambda DNA and by directly counting the radioactivity that remains associated with the beads after washing. The results of the capture reaction using a large lambda DNA genome (~50 kb) are shown in Table 3. The specificity of the reaction for the capture of biotinylated probe which was hybridized with double-stranded target was verified by including three control reactions (Table 3, reactions 2–4). These reactions showed that: (1) RecA-coated biotinylated probe was required for specific target DNA capture (reaction 1) since no significant signal was obtained in a reaction without RecA (reaction 2), (2) RecA inclusion in the reaction was not the cause of target capture because only background level DNA capture occurred in the presence of non-biotinylated non-homologous DNA probe coated with RecA (reaction 3), and (3) the average background, non-specific, target DNA capture was approximately 3.5% (reactions 2–4).

(ii) Signal amplification from captured DNA

A prototype protocol for detecting the bead-captured target DNA is described briefly below. For this step, captured target is released from the beads by heating in a reaction mix containing dNTP precursors, one or more of which is labeled (e.g. bio-14-dATP, or dNTP with a directly detectable label, such as FITC-11-dUTP, etc . . .) and a ss DNA primer (or primers) not homologous to the original capture probe sequences, but homologous only to target sequences, is (are) added and allowed to anneal to the single strands of target DNA. After annealing, the reaction is cooled and a DNA polymerase enzyme preferably, DNA polymerase T7 (SEQUENASE™ Version 2.0, USB) and appropriate buffer are added to allow DNA synthesis by primer extension. Alternatively, a high temperature polymerase could also be used and the reaction incubated at a temperature allowing processive DNA synthesis. During primer extension, labeled DNA precursor(s) is incorporated into the newly synthesized DNA strand(s). Because the DNA primer(s) is not homologous to the previously used RecA-coated probe(s), label incorporation specifically indicates the presence of the correct captured target. Use of a capture moiety either directly associated with the primer(s), such as poly(A), or able to be added later, allows subsequent capture of the amplified target signal on oligo(dT) attached to magnetic beads, cellulose, etc. Capture is followed by removal of unincorporated precursor label from the amplified DNA, and if necessary a blocking agent, such as, for example, I-Block (SOUTHERN-LIGHT™, Tropix) is used to block the non-specific binding of the detection moiety (e.g., AVIDx-AP™, Tropix) to the capture matrix. After blocking, substrate is added to allow specific signal detection from the amplified target DNA, and signal is detected by any appropriate means. A schematic outline of a homogeneous diagnostic double D-loop assay is shown as follows. Although a specific labeling, capture and detection scheme is presented, there are numerous ways in which such an assay could be practiced.

Figure 20C:
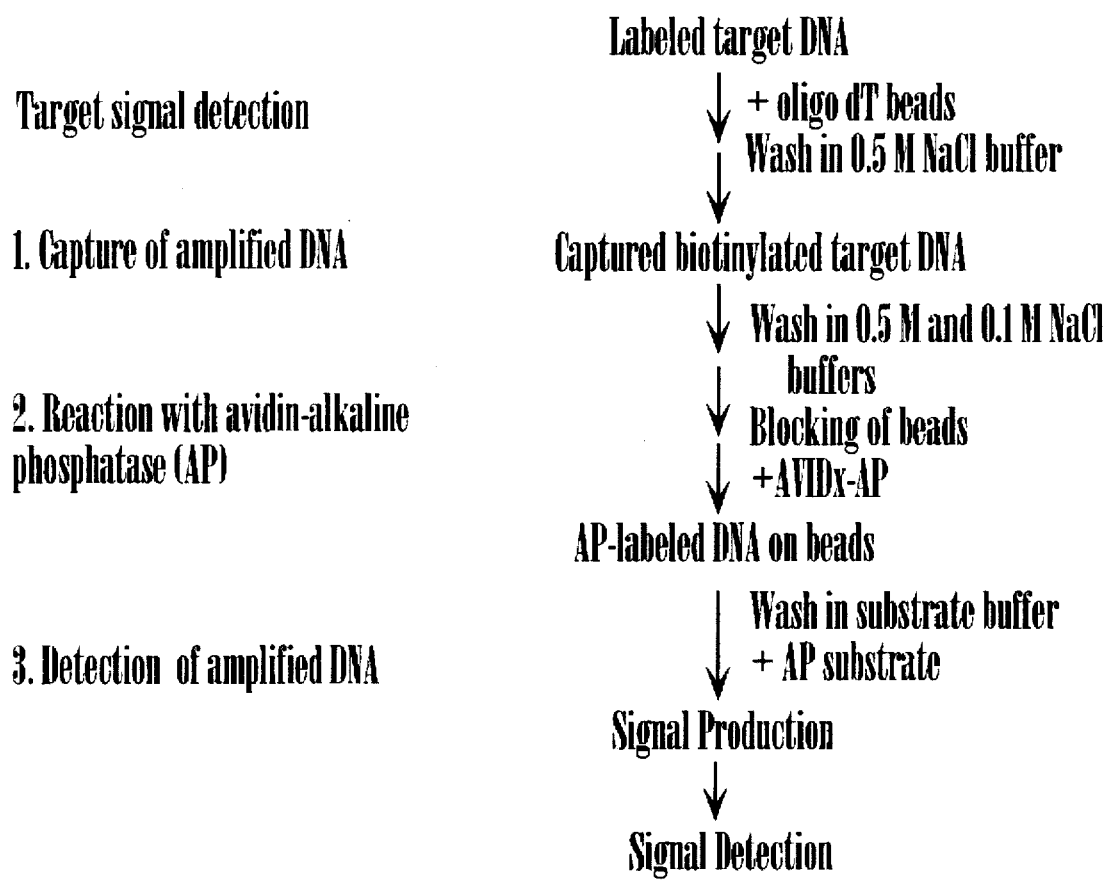

Schematic outline of a homogeneous diagnostic assay for duplex DNA targets with Double-D-loop hybrids is shown in FIGS. 20A and 20B.

The following examples illustrate, but in no way are intended to limit the present invention.

Materials and Methods

Restriction enzymes were obtained from Boehringer Mannheim (Indianapolis Ind.) or New England Biolabs (Beverly Mass.) and were used as per the manufacturer's directions.

Generally, oligonucleotides were radiolabeled with [γ-$^{32}$P]ATP and T4 polynucleotide kinase. Labelling reactions were performed in the buffers and by the methods recommended by the manufacturers (New England Biolabs, Beverly Mass.; Bethesda Research Laboratories, Gaithersburg Md.; or Boehringer/Mannheim, Indianapolis Ind.). Oligonucleotides were separated from buffer and unincorporated triphosphates using Nensorb 20 pre-formed columns (NEN-DuPont, Boston, Mass.) as per manufacturer's instructions, and subsequently dialyzed versus dd H$_2$O if necessary.

EXAMPLE 1

Preparation of RecA-coated Probes

A series of double- and single-stranded DNA probes and primers have been generated. The positions of these probes and primers relative to a contiguous 500 base pair region of the lambda phage genome are shown in FIG. 1: the nucleotide sequence of this region of the lambda genome is presented in FIG. 2. The base positions of the 5' and 3' ends of each probe and primer, relative to the lambda viral genome, are listed in Table 1.

TABLE 1

LAMBDA BASES DEFINING PROBE AND PRIMER DNA SEQUENCES

| Probe or Primer | Bases Included Sequence* | Size (bs) or (bp) |
|---|---|---|
| PCR01* | 7131–7155 | 25 |
| PCR02** | 7606–7630 | 25 |
| PCR03A* | 7351–7390 | 40 |
| DL80-1* | 7131–7210 | 80 |
| DL80-2** | 7131–7210 | 80 |
| DL80-3* | 7551–7630 | 80 |
| DL80-4** | 7551–7630 | 80 |
| 500 (ds) | 7131–7630 | 500 |
| 280 (ds) | 7351–7630 | 280 |
| 159 (ds) | 7472–7630 | 159 |
| 121 (ds) | 7351–7471 | 121 |
| Biotin-121* | 7351–7471 | 121 |
| 121-$^{32}$P** | 7351–7471 | 121 |
| 79 (ds) | 7552–7630 | 79 |
| Biotin-79* | 7552–7630 | 79 |

*5' strand.
**Opposite strand.

TABLE 2

BEAD CAPTURE OF PROBE:TARGET HYBRIDS SHOWS THAT THE RecA-CATALYZED DOUBLE D-LOOP PRODUCT CONTAINS TWO DNA PROBE STRANDS

| | | Probe Strand(s) | | $^{32}$P Radioactive DNA Counts Captured | |
|---|---|---|---|---|---|
| Reaction | RecA | Biotin (Capture DNA) | $^{32}$P (Radioactive Reporter DNA) | % Total Counts per Minute Expected* | Corrected % of Counts per Minute* |
| 1 | – | + | + | 4 | 0 |
| 2 | + | – | + | 11 | 0 |
| 3 | + | + | – | 0 | 0 |
| 4 | + | + | + | 110 | 98 |

*See FIG. 8 for explanation of sample reactions. Percentages were calculated from the $^{32}$P counts remaining on the DYNAL ™ streptavidin-coated beads after three washes of each capture reaction with 1X acetate reaction buffer. The total expected $^{32}$P counts per minute were determined by scintillation counting of DNA in minced gel slices from experiments identical to those in FIG. 8. Since no radioactive DNA was added to reaction 3 (containing biotin capture probe only), no radioactive counts were expected for this reaction.
†Radioactive $^{32}$P counts in DNA were corrected for nonspecific bead capture of background DNA counts (i.e., counts from reaction 2 without biotin capture probe).

Primers PCR01 and PCR02 correspond to the primers supplied in the "GENEAMP™" DNA Amplification Reagent Kit (Perkin Elmer Cetus, Norwalk Conn.).

Single-stranded primers (PCR01, PCR02 and PCR03A) and single-stranded probes (DL80-1 through 4, biotin-121, 121-$^{32}$P, and biotin-79) were chemically synthesized using commercially available phosphoramidite precursors on an Applied Biosystems 380B DNA synthesizer (Applied Biosystems, Foster City Calif.).

DNA molecules were biotinylated by reaction with a biotin phosphoramidite at the last 5' base (New England Nuclear-DuPont, Boston, Mass.) before deblocking. All chemically synthesized DNA molecules were deblocked according to the manufacturer's specifications.

Short DNA probes (25-mers) were used without further purification. Single-stranded 80-mer and 121-mer DNA probes were purified by polyacrylamide gel electrophoresis using 8%, and 5% or 8% polyacrylamide gels, respectively. Full sized DNA products were obtained by excising DNA bands from the gels that corresponded to the correct size DNA molecule. The DNA molecules were recovered from gel pieces by electroelution using the "ELUTRAP™" system (Schleicher and Schuell, Keene, N.H.). Both probes and primers were concentrated by standard ethanol precipitation (Maniatis et al.). Probe and primer DNA concentrations were determined based on UV absorbance at 260nm of the diluted DNA.

Double-stranded 500 and 280 bp regions of the lambda genome (FIG. 1) were synthesized using primers PCR01 and PCR02, or PCR03A and PCR02, respectively, Taq polymerase and standard DNA amplification reaction conditions (Perkin Elmer Cetus; Mullis; Mullis et al.). The amplification products were separated from the DNA primers by electrophoresis through a 0.7% agarose (Sigma Type II, Sigma, St. Louis Mo.) gel (500-mer) or a 4% "NUSIEV™E" (FMC BioProducts, Rockland, Me.) agarose gel (280-mer). The DNA molecules in the bands corresponding to the amplification products were electroeluted, concentrated, and their actual concentrations' determined as described above.

Double-stranded 121- and 159-mer probes were obtained by restriction digestion of purified 280-mer using the enzyme AluI (New England Biolabs, Beverly Mass.). The DNA probes were isolated by gel electrophoresis, electroeluted and concentrated as above.

Double-stranded 79-mer probe was obtained from restriction digestion of the purified 500-enzyme Hp the enzyme HpaII. The digestion products were separated and purified from uncut DNA by electrophoresis using either 3% or 4% "NUSIEVE" (FMC Bioproducts) gels or 1% agarose gels. Specific DNA fragments were recovered from the gels as described above.

Single-stranded or double-stranded DNA molecules were 5'-end-labeled (Maniatis et al.) with [γ-$^{32}$P]ATP and T4 polynucleotide kinase (Promega, Madison Wis.). When necessary, the DNA molecules were dephosphorylated with alkaline phosphatase (Boehringer Mannheim, Indianapolis Ind.) before labelling with T4 polynucleotide kinase. Un-incorporated label was removed using "NENSORB 20" nucleic acid purification columns (NEN-DuPont). The labeled DNA molecules could be further purified by dialysis against sterile double-distilled water followed by concentration by freeze-drying. $^{32}$P-labeled 121-, 159- or 79-mer were also obtained by the appropriate restriction enzyme digestion of $^{32}$P end-labeled 280-mer or 500-mer.

EXAMPLE 2

Purification of the Wild-Type RecA and Mutant RecA 803 Proteins

RecA and recA-803 proteins were isolated from the overproducing strains JC12772 and JC15369 (obtained from A. J. Clark and M. Madiraju). These strains contain the RecA and recA-803 coding sequences on plasmids present at high copy numbers per cell. Analysis of total protein from JC12772 and JC15369 cell extracts by SDS-polyacrylamide gel electrophoresis, under denaturing conditions, showed that the 38,000-dalton RecA or recA-803 protein is the major protein produced in these strains.

RecA and recA-803 proteins were purified by modification of established procedures (Shibata et al., 1981; Griffith et al., 1985) using fast protein liquid chromatography (FPLC) using a hydroxylapatite column obtained as a powder (BioRad) followed by an anion ("MONO Q™", Pharmacia) exchange column.

Protein purification was monitored as follows:
(i) identifying the 38,000-dalton RecA protein by SDS-PAGE ("PHASTGEL™" system, Pharmacia, Piscataway N.J.);
(ii) assay of the RecA ssDNA-dependent ATPase activity using [γ-$^{32}$P]ATP and single-stranded DNA (Shibata et al., 1981). The products of the reaction were separated using PEI cellulose thin-layer chromatography (EM Science, N.J.): the PEI plates were developed in a solvent of 0.5M LiCl and 0.25M formic acid. Products were detected by autoradiography.

(iii) assay of DNase activity. DNase activity was monitored by incubating the RecA protein samples with a mixture of phiX174 linearized and super-coiled circular double-stranded RF, and circular single-stranded DNAs in RecA strand-transfer buffer (Cheng et al., 1988) for 1 hr at 37° C. DNA nicking and digestion were monitored after deproteinization by visualizing the DNAs with ethidium bromide after agarose gel electrophoresis and comparing the quantities of each DNA type in the RecA incubated samples with those incubated in buffer without RecA. Only RecA protein samples showing no detectable DNase activity were used.

(iv) assay of D-loop activity with 500-mer oligonucleotide probe using a method modified from Cheng et al. (1988).

Silver stained SDS-polyacrylamide gel profiles of the final "MONO-Q"-purified RecA and recA-803 proteins showed a single 38,000-dalton band from each preparation that was essentially free of other cellular polypeptides.

EXAMPLE 3

RecA Protein Coating Reactions

RecA protein coating of probes was normally carried out in a standard 1× RecA coating reaction buffer (10× RecA reaction buffer: 100 mM Tris acetate (pH 7.5 at 37° C.), 20 mM magnesium acetate, 500 mM sodium acetate, 10 mM DTT and 50% glycerol (Cheng et al. 1988). All of the probes, whether double-stranded or single-stranded, were denatured before use by heating to 95°–100° C. for five minutes, placed on ice for one minute, and subjected in a Tomy centrifuge to centrifugation (10,000 rpm) at 0° C. for approximately 20 seconds. Denatured probes were added immediately to room temperature RecA coating reaction buffer mixed with ATPγS and diluent (double-distilled $H_2O$), as necessary.

This reaction mixture typically contained the following components: (i) 2.4 mM ATPγS; and (ii) between 10–40 ng of double-stranded probe. To this mixture either (i) one μl of RecA protein, usually at 5.2 mg/ml (purchased from Pharmacia or purified as described above), or (ii) an equivalant volume of RecA storage buffer (20 mM Tris-HCl pH 7.5, 0.1 mM EDTA, 1.0 mM DTT, and 50% glycerol) was rapidly added and mixed. The final reaction volume for RecA coating of probe was usually about 10 μl. RecA coating of probe was initiated by incubating probe-RecA mixtures at 37° C. for 10 min.

RecA protein concentrations in coating reactions varied depending upon probe size and the amount of added probe: RecA protein concentration was typically in the range of 6.8 to 51 μM. When single-stranded DNA probes were coated with RecA, independently of their complementary probe strands, the concentrations of ATPγS and RecA protein were each reduced to one-half of the concentrations used with double-stranded probes: that is, the RecA protein and ATPγS concentration ratios were kept constant for a given concentration of individual probe strands.

FIG. 3 shows an autoradiogram illustrating RecA protein binding to 121-mer and 159-mer DNA probes as measured by DNA band-shift assays. Heat denatured $^{32}$P-labeled double-stranded 121-mer and 159-mer DNA probes were reacted with RecA protein as described above. The final RecA-DNA reaction mixtures contained 2.4 mM ATPγS. RecA protein or RecA storage buffer was added to each of four reactions containing 0.01 μg of either denatured 121- or 159-mer DNA probe. The final concentration of RecA in each reaction was 0, 0.137, 1.37 or 13.7 μM in lanes 1 and 5, 2 and 6, 3 and 7 or 4 and 8, respectively (FIG. 3). All RecA/DNA probe coating reactions were performed in a final volume of 10 μl. RecA binding was initiated by incubating all the reactions at 37° C. for 10 min. Five μl aliquots of each reaction were loaded into a 2% agarose gel in 1× TBE buffer and electrophoresed at 9.2 v/cm for 2 hours. A HaeIII digest of ΦX-174 DNA (GIBCO-BRL, Gaithersburg Md.) served as a double-stranded DNA size marker (M). Marker DNA was 5' end-labeled with $^{32}$P as described above. The gel was air dried on saran wrap in a Bioscycler oven at 65° C. The dried gel was then exposed to X-ray film.

As can be seen from FIG. 3, retardation of the electrophoretic mobility of the DNA probes increases with increasing RecA concentration.

The same conditions as described above were employed for recA-803 protein.

EXAMPLE 4

Formation of RecA Protein-Mediated Multiplexes

Probe coating reactions were performed as described in Example 3. After the coating reactions were complete target DNA was added to each reaction. The target DNA was derived from the lambda viral genome and if restriction enzyme digested, contained DNA fragments homologous to the probe sequence and non homologous ones as well. Typically, 0.66–1.5 μg of target DNA was added to each reaction in 1× reaction buffer. The magnesium ion concentration of the total reaction was adjusted to 12 mM by addition of an aliquot of 0.2M magnesium acetate. Final reaction volumes were usually 20 μl after the addition of the target DNA.

Probe target mixtures were incubated at 37° C. to allow RecA catalyzed homologous probe:target reactions. After incubation for 60 minutes the reactions were deproteinized with proteinase K (10 mg/ml) at 37° C. for 15–20 min, followed by the addition of sodium dodecylsulfate (SDS) to a final concentration of 0.5–1.2% (w/v). Aliquots of each reaction were loaded into wells of 0.7–1.0% agarose gels after addition of tracking dye (Maniatis et al.). The gels were electrophoresed either at room temperature or at 4° C. The gels were stained with ethidium bromide and DNA molecules visualized by UV light. The gels were photographed using a red filter and Polaroid 667 black and white film.

When radiolabeled DNA probes were utilized in the reactions, the probe:target complexes were detected by autoradiography of either wet or dried agarose gels using either DuPont CRONEX QUANTA III™ or LIGHTENING PLUS™ intensifying screens and Kodak X-OMAT AR5™ film. For signal quantitation, target DNA bands showing signal on autoradiograms were excised from gels, crushed, suspended in scintillation cocktail (AQUASOL-2™, DuPont-NEN, Boston Mass.), and the radioactivity counted in a Packard 2000 CA Tri-Carb liquid scintillation analyzer.

Double-stranded 280-mer and 500-mer probes (Table 1) were reacted with a double-stranded linear target DNA fragment (8370 bp lambda DraI digest fragment that contains each probe sequence) as described above. Denatured probe DNA molecules were coated with RecA protein in the presence of 2.4 mMATPγS and 34.2 μM RecA protein. Denatured probes that were not coated with RecA protein were added to the same reaction conditions minus the RecA protein. After incubation for 10 min at 37° C., 0.66 μg of lambda genomic DNA, which had been digested with the restriction enzyme DraI, was added to each probe mixture:

the genomic DNA was suspended in 1× reaction buffer with an adjusted Mg$^{++}$ concentration, as described above. The final micromolar ratio of double-stranded probe to homologous double-stranded target fragment was 10.6:1 for 500-mer and 21.6:1 for 280-mer. Incubation of the probe:target reactions were carried out as described above.

The reactions were deproteinized and loaded into a 0.7% agarose gel. The DNA was subjected to electrophoresis to separate the probe and target DNA fragments. A photograph of the ethidium bromide stained DNA in the gel containing these reactions is shown in FIG. 4A. The three reactions on the left side are control reactions using pUC18 double-stranded circular DNA target and RecA coated single-stranded 69-mer probe (these control substrates were provided by B. Johnston, SRI, Menlo Park, Calif.). The center lane contained 1 kb marker DNA (GIBCO-BRL). The four reactions on the right side of the gel were the lambda DraI digest target DNAs.

This gel was dried and exposed to X-ray film as described above. The resulting autoradiogram is shown in FIG. 4B. Both RecA coated 500-mer and 280-mer probes specifically hybridized with the correct DraI lambda DNA digest target fragment. The position of probe:target DNA homology is at least 832 bp from the 3' end of the 8370 bp target fragment. This result demonstrates the formation of 500-mer and 280-mer RecA-facilitated DNA hybridization products that are stable to deproteinization. Generation of these stable DNA complexes requires RecA protein.

EXAMPLE 5

Stable Complex Formation Between Small Double-Stranded Probes and Linear Double-Stranded Target DNAs This example describes the use of small double-stranded probes to generate complexes with linear double-stranded DNA that are stable to deproteinization.

The following hybridization reactions were carried out as described in Example 4. All RecA protein-coating reaction volumes were 10 µl. Each reaction contained 2.4 mM ATPγS and 20.5 µM RecA, unless otherwise noted. Final reactions contained 1.3 µg DraI digested lambda DNA. The following reaction conditions correspond to lanes in FIGS. 5A and 5B: Lanes 1 and 2, 280-mer probe with and without RecA protein, respectively; lane 3, 121-mer probe with RecA protein; lanes 4–6, 79-mer probe with RecA protein. The reactions in lanes 5 and 6 contained RecA protein concentrations of 8.54 and 41 µM during the RecA probe coating reaction. The reactions were deproteinized and loaded into a 0.7% agarose gel. The gel was subjected to electrophoresis to separate the probe and target DNA fragments.

FIG. 5A shows a photograph of ethidium bromide stained DNA in an agarose gel showing the lambda DraI digest target fragments from the above reactions. FIG. 5B shows an autoradiograph of the DNA in an agarose gel shown in FIG. 5A. The arrows indicate the migration position of the DraI lambda target fragment homologous to the probes used. The results indicate that complexes stable to deproteinization can be achieved with all of the RecA-coated DNA probes: 280-mer, 121-mer, and 79-mer. As above, the stable complexes were formed at least 832 bases from the end of a linear double-stranded DNA target molecule.

EXAMPLE 6

Stable Complex Formation Requires a Double-Stranded Probe

A. Requirement for a Double-Stranded DNA Probe.

RecA-coated DNA probes were used for hybridization with 3.0 µg of lambda DraI digested target DNA per reaction (60 minutes) as described in Example 4. Two chemically synthesized single-stranded DNA 121-mers were used. The strands were complementary to each other. One strand was biotin-labeled and the other $^{32}$P-labeled.

The following reaction numbers correspond to lanes in FIGS. 6A and 6B. Reactions 1, 2, 5, 6 and 3, 4 contained 2.4 mM or 4.8 mM ATPγS, respectively. All reactions used 20 ng of the $^{32}$P-labeled DNA probe strand and 10.4 µg RecA protein: each reaction contained the same $^{32}$P-specific activity. Reactions 3–6 also contained the biotin labeled strand. In reactions 3 and 4, both DNA probes were added to the initial 10 µl RecA reactions at the same time. For reactions 5 and 6, the $^{32}$P- and biotin-labeled probes were each coated with RecA in separate 10 µl reactions, then one-half of each reaction mix was incubated with target DNA for 30 min before addition of the missing complementary RecA coated DNA probe strand. The $^{32}$P-labeled DNA strand was added first to reaction 5 and second to reaction 6.

All reactions were deproteinized with proteinase K and SDS before electrophoresis. FIG. 6A shows a photograph of ethidium bromide stained DNA in an agarose gel showing the lambda DraI digest target fragments from the above reactions. The reaction conditions are summarized in FIGS. 6A and 6B. The autoradiogram of the air dried gel of FIG. 6A is shown in FIG. 6B.

Two DNA probe strands are required for the production of stable deproteinized products formed at a homologous internal sequence on linear target DNA (lanes 3, 5, and 6, compare lane 2). RecA protein is also required for product formation (lanes 3, 5 and 6, compare lane 4).

B. A Model of the Double-Stranded Stable Product.

FIG. 7 shows a possible model for the deproteinized double-stranded RecA catalyzed hybridization product. FIG. 7 illustrates a stable double D-loop mutliplex formed with short end-labled DNA probes and a double-stranded linear DNA target. The model shown depicts hybridization on the 8370 bp DraI DNA lambda target, where probe:target homology begins at least 832 bases from the short end of the target (3' end with respect to the whole lambda genome). The DraI fragment includes lambda bases 93–8462. The exact regions of homology are defined by Table 1. A single-stranded RecA protein coated probe does not yield complexes that are stable to deproteinization (see FIG. 6B above).

EXAMPLE 7

Probe:Target Capture and DNA Detection

A. Hybridization Reactions.

Complementary 121-mer DNA probes (Table 1) were individually chemically synthesized. The complementary strands were differentially labeled using [γ-$^{32}$P]ATP and biotin (the reporter and capture moieties, respectively). All probe coating reaction mixes contained 2.4 µM ATPγS, 20 ng single-stranded probe, 5.2 µg of RecA protein (5.2 µg/µl; Pharmacia), or an equivalent to volume of RecA storage buffer (without RecA protein), per 10 µl reaction. For experiments using both biotin- and $^{32}$P-labeled probes (reactions 1 and 4), 10 µl aliquots of the analogous biotin- or $^{32}$P-labeled probe-coating reactions were mixed together (to give 20 µl) before these mixtures were added to the target DNA mix. To keep all reaction volumes constant, reactions with only one single-stranded probe strand (reactions 2 and 3) used 10 µl of probe mix, 10 µl of probe reaction buffer (i.e., no second probe) and 20 µl of target DNA mix.

A lambda target DNA mix was prepared as follows: 1× RecA reaction buffer, 1 to 10 dilution of 0.2M stock Mg acetate, and ApaI digested lambda DNA. Twenty microliters of the target DNA mix was added to each of the 20 μl probe reaction mixtures. These reactions were incubated for 60 minutes at 37° C. The 40 μl reactions were deproteinized, divided into two equal aliquots, the two aliquots loaded in adjacent wells in a 0.7% agarose gel and the components fractionated by electrophoresis (as described above).

The initial specific activity of all reactions containing the $^{32}$P-labeled strand (1, 2 and 4) were identical. The ethidium bromide stained gel with adjacent duplicate lanes of each reaction is shown in FIG. 8. The contents of each reaction are summarized in FIG. 8.

The portion of each lane of the gel corresponding to the 10.1 kb lambda target DNA (FIG. 8) was excised from the gel. Each excised fragment was placed into a microcentrifuge tube and rapidly frozen using dry ice. The DNA contained in each gel fragment was recovered by squeezing the frozen gel between folded parafilm until no more liquid was extruded. This DNA-containing liquid was then carefully removed with an EPPENDORF™ micropipette.

B. The Capture/Detection Assay.

The presence of two probe strands on the same target molecule (one biotin-labeled and the other $^{32}$P- labeled) was assayed by capturing biotin-containing-probe:target hybrids on streptavidin-coated paremagnetic beads (Dynal, Oslo, Norway). The manufacturer's bead storage buffer was removed before use. The beads were washed in 1× RecA reaction buffer, in 10× RecA reaction buffer, and finally in RecA reaction buffer. Before DNA capture, equal aliquots of washed beads were added to individual 1.5 ml microcentrifuge tubes and the final wash buffer was removed. Liquid was removed from all bead suspensions by placing microcentrifuge tubes containing the bead mixtures in a magnetic separating rack (Promega, Madison Wis.).

The DNA-containing reaction samples from above were each added to a microcentrifuge tube containing an aliquot of the washed paremagnetic beads. The samples were mixed, and incubated at room temperature for 15 min. Since beads settle with time, the mixtures were shaken several times during incubation to insure efficient biotin:streptavidin exposure. After the capture reaction, i.e., the binding of streptavidin to biotin, the paramagnetic beads in each reaction were amassed with a magnet and the reaction liquid removed.

Each sample of beads was washed three times with 1× RecA reaction buffer. The presence of $^{32}$P-labeled probe strand was assessed by adding liquid scintillation counting fluor to the beads and counting the radioactivity of the DNA captured by each bead reaction. These data are presented in Table 2.

TABLE 2

BEAD CAPTURE OF PROBE:TARGET HYBRIDS SHOWS THAT THE RecA-CATALYZED DOUBLE D-LOOP PRODUCT CONTAINS TWO DNA PROBE STRANDS

| | | Probe Strand(s) | | $^{32}$P Radioactive DNA Counts Captured | |
|---|---|---|---|---|---|
| Reaction | RecA | Biotin (Capture DNA) | $^{32}$P (Radio- active Reporter DNA) | % Total Counts per Minute Expected* | Corrected % of Counts per Minute[3] |
| 1 | − | + | + | 4 | 0 |
| 2 | + | − | + | 11 | 0 |
| 3 | + | + | − | 0 | 0 |
| 4 | + | + | + | 110 | 98 |

*See Figure 8 for explanation of sample reactions. Percentages were calculated from the $^{32}$P counts remaining on the Dynal ™ streptavidin - coated beads after three washes of each capture reaction with 1X acetate reaction buffer. The total expected $^{32}$P counts per minute were determined by scintillation counting of DNA in minced gel slices from experiments identical to those in Figure 8. Since no radioactive DNA was added to reaction 3 (containing biotin capture probe only), no radioactive counts were expected for this reaction.
†Radioactive $^{32}$P counts in DNA were corrected for nonspecific bead capture of background DNA counts (i.e., counts from reaction 2 without biotin capture probe).

In Table 2 percentages were calculated from the $^{32}$P radiolabelled DNA counts minute remaining on the DYNAL™ streptavidin-coated beads after three washes of each capture reaction with 1× acetate reaction buffer. No $^{32}$P-labeled DNA was added to reaction 3, which contains biotin capture probe only: no radioactive DNA counts were expected for this reaction. The "Total Expected Counts" in Table 2 were determined as follows. Identical reactions were performed as described above and the products separated by agarose gel electrophoresis. Gel fragments corresponding to the 10.1 kb target DNA were excised from the gel, minced, and placed in AQUASOL®. The amount of $^{32}$P-labeled DNA present in the samples was determined by liquid scintillation counting.

The results indicate that the hybridization product, containing two complementary but differentially labeled probes, can be captured using the streptavidin interaction with the biotin labeled probe strand and subsequently detected by a label in the complementary probe strand.

This bead capture of stable probe:target hybrids supports that homologous probe:target complexes catalyzed by RecA protein actually contained two homologous probe strands on the same double-stranded target molecule.

EXAMPLE 8

RecA+ Facilitated DNA Amplification Without Target DNA Denaturation

Reaction conditions for RecA protein facilitated DNA amplification have been described in co-pending and co-owned Ser. No. 07/520,321, for "PROCESS FOR NUCLEIC ACID HYBRIDIZATION AND AMPLIFICATION," filed 7 May 1990, herein incorporated by reference.

Double-stranded probe/primer pairs corresponding to DL801/2 and DL803/4 (Table 1) were denatured and coated with RecA protein as described above. To ensure that elongation of DNA primers occurs in only the desired direction, the 3'-ends of the appropriate primers can be terminated by a 2',3'-dideoxynucleotide. The dideoxynucleotide lacks the 3-hydroxyl group present in the conventional dNTPs. The absence of the hydroxyl group inhibits extension by preventing, the formation of a phosphodiaster bond between the dideoxynucleotide and the succeeding conventional dNTP. The addition of the dideoxynucleotide to the primer can be achieved by using the enzyme terminal deoxynucleotide transferase (Pharmacia, Piscataway, N.H.).

The probes are then allowed to react with the target DNA as described above. The product of the above reaction, consisting of two sets of double D-loops, is then used as the substrate in a typical DNA amplification reaction. The DNA reaction can be carried out in buffer containing 10 mM Tris-HCl (pH 7.5), 8–12 mM $MgCl_2$, and 50 mM NaCl supplemented with 200–750 μM dNTPs and DNA polymerase (e.g., exonuclease-free, DNA polymerase I, Klenow, or T7 DNA polymerase). In addition, the reaction may be supplemented with other enzymes or proteins (e.g. DNA helicase, topoisomerase, DNA ligase and single-strand binding (SSB) protein) which may facilitate the formation of the specific amplification product. The reaction is allowed to proceed for as long as necessary at 37° C. Upon termination, samples could be deproteinized (SDS, Proteinase K and/or phenol extracted) and analyzed by gel electrophoresis. After electrophoretic separation, the resulting amplified DNA can be visualized by either ethidium bromide staining of the DNA in the gel or by DNA hybridization with a target specific DNA probe. Alternatively, amplification DNA probes could be biotinylated and the newly synthesized DNA captured by appropriate means and then reported and detected as previously described.

DNA synthesis reactions are initiated by the addition of 1–2 unit(s) of exonuclease-free *E. coli* DNA polymerase I (U.S. Biochemicals) and 750 μM of each dNTP. The reactions are maintained at 37° C.

Following the initial addition of polymerase, the reactions can be supplemented with 1 unit of e.g., Klenow and/or additional dNTPs, at specific intervals spaced over the time course of the reaction.

Samples are treated with proteinase K, before being loaded for electrophoretic separation. After electrophoretic separation the resulting amplified DNA fragments can be visualized by either ethidium bromide staining of the gel or by hybridization with a target specific probe.

For hybridization analysis the gel can be transferred by standard protocols (Maniatis et al.) onto hybridization transfer membrane (Hybond-N, Amersham). The DNA is UV cross-linked (Stratolinker, Stratagene) to the membrane. The UV-treated transfer membrane is hybridized with end-labelled (Boehringer Mannheim) probe PCR03A (Table 1): PCR03A (nucleotides 7351 through 7390 of the native lambda genome) is a 40-mer corresponding to an internal DNA sequence of the 500 base pair lambda template that is the target of the above amplification reaction. The membrane is subjected to autoradiography.

EXAMPLE 9

In situ DNA Detection Utilizing the Double D-loop Reactions

A. Preparation of Probe Complex.

Biotinylated chromosome X alpha satellite DNA probe is obtained from ONCOR (Gaithersburg, Md.). Alternatively, probes can be biotinylated by standard nick-translation methods or by polymerase chain reaction (Weier et al., 1990).

The double-stranded probe diluted in sterile $ddH_2O$ to the desired concentration prior to denaturation, is denatured in a 0.5 ml microcentrifuge tube in a 100° C. heat block for 5 minutes. The tube is immediately placed in an ice water bath for 1 to 2 min followed by a brief centrifiguration at 4°–6° C. in a TOMY™ microcentrifuge, and the tubes are returned to an ice water bath. Approximately 5 minutes prior to addition of denatured DNA probe to the hybridization mixture the tube containing the probe is placed in ice in a freezer at –20° C. The probe hybridization mixture contains the following-components in a broad range of concentrations and is combined in the order listed: 1 μl of 10× RecA reaction buffer [10× RecA reaction buffer:100 mM Tris acetate pH 7.5 at 37° C., 20 mM magnesium acetate, 500 mM sodium acetate, 10 mM DTT and 50% glycerol (Cheng et al., 1988)]; 1.5 μl ATPγS from 16.2 mM stock) (Pharmacia) [GTPγS, rATP (alone or in the presence of a rATP regenerating system), dATP, mixes of ATPγS and rATP, or mixes of ATPγS and ADP, may also be used in some reactions]; 0.75 μl 20 mM magnesium acetate; 4–60 ng (or more in some reactions) of denatured probe in sterile water; 1.25 μl 0.137 mM stock RecA protein when purchased from Pharmacia [when obtained from other sources or prepared in the laboratory the amount (μl's) added varies according to concentration of stock].

The mixture is incubated at 37° C. for 10 minutes followed by addition of 0.5 μl/reaction of 200 mM magnesium acetate. Final concentrations of reaction components are: 4.0 mM to 10 mM Tris acetate, 2.0 mM to 15 mM magnesium acetate, 20.0 mM to 50 mM sodium acetate, 0.4 mM to 1.0 mM DTT, 2% to 5% glycerol, 1 mM to 2.5 mM ATPγS, 0.005 mM to 0.02 mM RecA protein.

B. Preparation of HEp-2 Fixed Cell Nuclei.

HEp-2 cells were originally derived from human male larynx epidermoid carcinoma tissue. HEp-2 is a chromosome ploidy variable cell line (Chen).

The cells are cultured for 24 hours after seeding in DMEM medium (Whittaker or Gibco-BRL) supplemented with 10% FBS, sodium pyruvate and a penicillin/ streptomycin antibiotic mix at 37° C. under standard conditions. Cells are pelleted by low-speed centrifugation and the pellet is resuspended in 75 mM KCl in a 37° C. water bath for between 5 and 15 minutes for the desired amount of nuclear swelling to occur, followed by cell fixation accomplished by the addition of 3:1 ice cold methanol:acetic acid and centrifugation at 6° C.

One ml of fluid is left in the tube with the pelleted cells, additional ice cold methanol:acetic acid is added, and the cells mixed by gentle mixing of the tube, followed by centrifugation. Repeated additions of methanol-acetate degrades cytoplasm (HEp-2 and other cell types may be fixed in alternative ways, some of which do not degrade cytoplasm.)

Preparations of isolated nuclei are fixed by resuspension in 3:1 methanol:acetic acid at a concentration ~$2\times10^6$/ml and is either dropped by pipette in 10 μl aliquots onto clean glass slides which are strored at –20° C. or the suspended nuclei are stored at –20° C. for later use.

C. Hybridization Reactions for Fixed Preparations.

Ten μl of probe mixture/reaction from Example 9A is applied to the fixed preparation on glass slides. Glass coverslips are placed over the hybridization areas and sealed with rubber cement, and reactions are incubated in a moist container in a 37° incubator for between 1–4 hours.

Following incubation, the rubber cement is manually removed and the slides are washed in coplin jars 3 times for 10 minutes each in 2× SSC (20× SSC: 3NaCl, 0.3M sodium citrate, pH 7.0 is used in all SSC containing preparations in these assays) in a water bath at 37° C. Other washing conditions may also be employed.

The slides are placed in pro-block solution [4× SSC, 0.1% TRITON®X-100, 5% Carnation nonfat dry milk, 2% normal goat serum (Gibco), 0.02% sodium azide, pH 7.0] for 25 minutes at room temperature (RT), followed by immersion in 5 ug/ml FITC-avidin DCS cell sorter grades (Vector, A-2011) in preblock solution for 25 minutes at room temperature. The slides are successively washed in 4× SSC, 4× SSC and 0.1% TRITON®X-100, and 4× SSC for 10 minutes each at room temperature, followed by brief rinsing in double-distilled water. The slides are then dried.

Antifade solution is applied to the slides [100 mg p-phenylenediamine dihydrochloride (Sigma P1519) in 10 ml phospate buffered saline, adjusted to pH 8 with 0.5M carbonate-bicarbonate buffer (0.42 g $NaHCO_3$ adjusted to pH 9 with NaOH in 10 ml $ddH_2O$) added 90 ml glycerol, and 0.22 um filtered], and coverslips are placed over the preparations. Anitifade containing a counterstain such as propidium iodide or DAPI solution can be used instead of anitifade alone.

If necessary, signal amplification is performed as follows: Slides are washed for 5–10 minutes in 4× SSC and 0.1% TRITON®X-100 at RT to remove coverslips and antifade, followed by incubation in preblock solution for up to 20 minutes. The slides are then incubated with biotinylated goat anti-avidin antibody (Vector BA-0300) at a concentration of 5 ug/ml diluted in pre-block solution for 30 minutes at 37°20 C. Slides are successively washed for 10 minutes each in 4× SSC, 4× SSC and 0.1% TRITON® X-100 4× SSC at RT, then immersed in preblock solution for 20 minutes at RT, then immersed in preblock solution with 5 ug/ml FITC-avidin for 20 minutes at RT. Slides are again washed in the 4× SSC series, briefly rinsed in $ddH_2O$, and on slides mounted with an antifade or antifade with counterstain.

Specific signals detected using standard fluorescence microscopy observation techniques.

D. Dectection of Specific Chromosome Sequences in Fixed Nuclei and Whole Cells.

The hybridization mixture is combined in the following order: 1 µl 10× RecA reaction buffer, 1.5 µl ATPγS (16.2 mM stock, Pharmacia), 0.75 µl magnesium acetate (20 mM stock), 12 µl (Example 8A) containing 20 to 60 or more ng of danatured probe in $ddH_2O$, RecA (0.137 mM stock, Pharmacia). The mixture is incubatad in a 37° C. water bath for 10 minutes followed by addition of 0.5 µl 200 mM magnesium acetate.

EXAMPLE 10

RecA Mediated Double D-loop Hybridization Reactions Using a Variety of Cofactors This example describes the formation of the double-D-loop complex using a number of different cofactors for the RecA protein coating reactions.

Double-D-loop reactions were carried out in 1× D-loop buffer (10× buffer: 100 mM Tris acetate (pH 7.5 at 37° C.), 20 mM magnesium acetate, 500 mM sodium acetate, 10 mM DTT and 50% glycerol (Cheng et al. 1988)) using 38 ng probe and containing ATPγS (Pharmacia), rATP (Pharmacia), dATP (USB) or GTPγS (Pharmacia) at a concentration of 1.2 mM. The reactions were established with or without a regenerating system and contained 1.2 µg λ/ApaI target DNA digest (New England Biolabs, Beverly Mass.). The probe was the Lambda 280-mer (Table 1) end-labeled with $^{32}P$ (Ausubel, et al.). The Lambda target fragment, i.e., the ApaI fragment containing sequences homologous to the probes, is the smaller 10.1 kb fragment indicated by an arrow in FIG. 16. The final concentration of RecA in all RecA containing reactions was 12.3 mM. Typically, the final magnesium acetate concentration was approximately 12 mM in each reaction (Example 4).

The double-D-loop formation reactions were deproteinized using 10 mg/ml proteinase K and 0.5% SDS. The deproteinized RecA mediated double D-loop hybridization reactions containing heat denatured 280-mer probe and different cofactors described above, were resolved by electrophoresis on an agarose gel. The gel was stained with ethidium bromide (Maniatis, et al.) and a photograph of the gel is shown as FIG. 16. The gel was dried and exposed to X-ray film.

Figure 16:
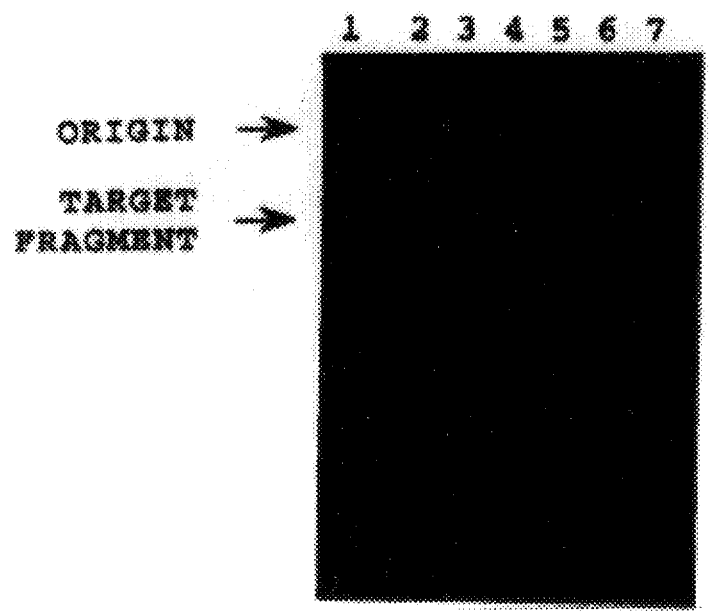
FIG. 16 shows an ethidium bromide stained agarose gel on which the components of deproteinized RecA mediated double D-loop hybridization reactions, using heat denatured 280-mer probe and different cofactors, were resolved by electrophoresis.
Figure 17:
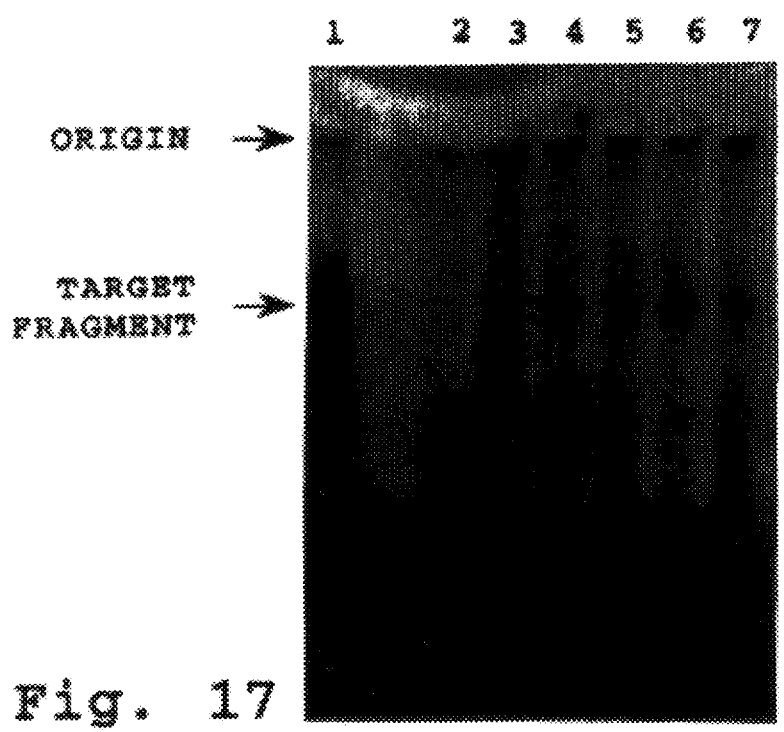
FIG. 17 shows an autoradiogram of the gel shown in FIG. 16, after drying.

FIG. 17 is an autoradiograph of the dried gel shown in FIG. 16. In FIG. 17, the lanes correspond to the following reaction conditions. RecA: lane 2, no RecA; lanes 1, 3–7, +RecA. Cofactors: ATPγS, lanes 1 and 2; rATP, lanes 3 and 4; dATP, lanes 5 and 6; GTPγS, lane 7. Lanes 3 and 5 also contained an ATP regenerating system [6 mM creatine phosphate, 10 U/ml phosphocreatine kinase (Sigma, St. Louis Mo.) and 100 mg/ml BSA (Promega, Madison Wis.)]. All reaction conditions were as described above.

The sample origin is indicated in FIGS. 16 and 17. As can be seen from the results presented in FIG. 17, stable double D-loop complexes were formed in the presence of each cofactor, as indicated by the labeled bands corresponding to the location of the 10.1 kb lambda target fragment (arrow).

EXAMPLE 1

RecA Mediated Double D-Loop Hybridization Reactions Containing ATPγS or a Mixture of ATPγS and rATP This example describes the formation of the double-D-loop complex using ATPγS and mixtures of ATPγS/rATP as cofactors for the RecA protein coating reactions.

The reaction conditions were as described in Example 10. FIG. 18 shows the photograph of an ethidium bromide stained agarose gel on which components of deproteinized RecA mediated double D-loop hybridization reactions, using 20 ng heat denatured 500-mer probes (Table 1), were resolved by electrophoresis. The probes were end-labeled with $^{32}P$ as above. The gel was dried and exposed to X-ray film.

FIG. 19 shows an autoradiograph of the dried gel in FIG. 18. In FIG. 19, the lanes correspond to the following reaction conditions. Lanes 1, 3 and 5—ATPγS cofactor (1.2 mM). Lanes 2, 4 and 6—a combination of ATPγS and rATP cofactors (0.73 mM and 0.5 mM, respectively). Lanes 1, 2 and 3, 4—reactions done with two different lots of λ/ApaI target DNA digest (New England Biolabs). Reactions in lanes 5 and 6 used a λ/DraI target DNA digest. 7A reactions contained 3.5 µg of target DNA mixture. RecA concentrations in all reactions were 6.85 µM. All concentrations are based on a final volume of 20 µl. All reaction conditions were as above.

The sample origin is indicated in FIGS. 18 and 19. As can be seen from the results presented in FIG. 19, stable double D-loop complex were formed in the presence of each cofactor, as indicated by the labeled bands corresponding to the location of the 10.1 kb and 8.4 kb lambda target fragments (arrows).

While the invention has been described with reference to specific methods and embodiments, it will be appreciated that various modifications and changes may be made without departing from the invention.

EXAMPLE 2

A homogeneous diagnostic assay

A. Labeling of lambda DNA

To facilitate evaluation of the capture reaction, lambda DNA (BRL), heated to 65° C. for 5 min, was end-labeled with $^{32}$P label using a Klenow fill-in reaction. The labeling reaction contained 10 µl 10× Klenow buffer (50 mM Tris HCl pH 7.5, 5 mM MgCl$_2$, 10 mM β-mercapto-ethanol) 18.3 µl 0.82 µg/µl lambda DNA, 2 µl 5 U/µl Klenow DNA polymerase (Pharmacia) and 56.7 µl dd H$_2$O. After incubation a 37° C. for 30 min the reaction was spun through a SEPHADEX® G-50 (Pharmacia) column in a 1 ml syringe. Labeled DNA was precipitated in ethanol in the presence of 0.3M NaOAc, resuspended in 20 mM Tris-HCl pH 7.5, 0.1 mM EDTA (TE) and then ethanol precipitated a second time. The dried DNA concentration was resuspended in 45 µl TE buffer. The DNA concentration was determined by its absorbance at 260 nm in a spectrophotometer.

B. DNA Probe synthesis and biotinylation

A 1000 bp region of the lambda genome was synthesized using standard protocols for thermally cycled PCR. The reaction used two chemically synthesized primers PCRO2 and PCRO1000 SEQ ID NO: 13 including bases 6631 to 6655 on the lambda genome), all four dNTP precursors and Taq DNA polymerase (Promega). Synthesized 1000-mer DNA (including lambda bases 6631 to 7630) was centrifuged through a Sephadex G-50 (Pharmacia) column and the DNA recovered by ethanol precipitation (2×). The 1000-mer DNA was resuspended in TE buffer, and its concentration was determined by OD measurement at 260 nm and varified with the DNA DIPSTICK™ (Invitrogen). Purified 1000-mer was then labeled with bio-14-dATP (Gibco-BRL) using the BRL. Nick Translation System. By slightly modifying the BRL protocol and adding twice the recommended amount of enzyme mix and incubating at 15°–16° C. for 1 hr 15 min, DNA probes with an average single-strand size of 300–500 bases were obtained. Nick-translated probes were precipitated in 0.3M NaOAc in ethanol and after resuspension in TE, DNA concentration was determined with the DNA Dipstic™ (Invitrogen).

C. RecA-coating of probes and probe:target hybridization

The single-stranded nick-translated probe was coated with RecA protein in a reaction mixture containing 1 µl of 10× acetate reaction buffer (Cheng et al, 1988) 1.5 µl of 3.24 mM ATP$_γ$S (Sigma) 0.6 µl of recA (2.76 µg/µl), 4.4 µl of sterile ddH$_2$O, and 2 µl of heat denatured DNA probe (15 ng/µl). The DNA probe was heat denatured at 100° C. for 5 min, quick-cooled in an ice-water bath, centrifuged at 4° C. in a Tomy microcentrifuge for 20 sec to collect the liquid, and then the proper aliquot was immediately added to a mixture containing the other reaction components. The total volume of the RecA-coating reaction mix after probe addition was 10 µl. The probe mix was incubated at of each cofactor, as indicated by the labeled bands 37° C. for 15 min followed by addition of 10 µl of a lambda target DNA mix containing 4 µl of 10× acetate reaction buffer, 4 µl of 0.2M Mg(OAC)$_2$, 4 µl of $^{32}$P-labeled whole duplex lambda DNA (280 ng/µl; previously heated at 65° C. for 5 min) and 28 µl of ddH$_2$O. The RecA-mediated hybridization reaction was incubated at 37° C. for 60 min, then 1.3 µl of 300 mM EDTA (pH 8.0) was added to give a final concentration of −20 mM. This was followed by addition of 21 µl of 20 mM Tris-acetate buffer pH 7.5 with 1M NaCl, to give a final salt concentration of 0.5M. Three control reactions were run along with the RecA reaction containing lambda probe. The first control reaction was identical to the RecA reaction except that it did not contain RecA protein and instead, an equivalent amount of RecA storage buffer was added. The two other control reactions were identical to the experiments containing lambda probes except that the lambda probes were replaced by an equivalent amount of nonlabeled, nick-translated φx174 DNA RFI DNA (NEBiolabs). Approximately 5 min before use, 300 ml of DYNA-BEADS® (Dynal) were washed three times in 20 mM Tris-acetate pH 7.5, 1M NaCl. Wash buffer was removed by amassing the beads in a magnetic separating rack (Promega) and each hybridination reaction (in 0.5M NaCl) was added to a separate aliquot (100 µl) of washed beads in a microcentrifuge tube and incubated with beads at room temperature for 30 min, with occasional gentle shaking of the tubes to carefully resuspend the beads in the reaction liquid. After capture, the liquid was removed and the beads were washed 3× with 100 µl 20 mM Tris-acetate pH 7.5, 1M NaCl.

The radioactivity on the beads and in the washes was determined by counting in SAFETY-SOLVE™ (RPI Corp.) in a Packard Scintillation counter. The results of these experiments are shown in Table 3.

TABLE 3

The double D-loop hybridization reaction with RecA-coated biotinylated complementary lambda DNA probes allows the specific capture of double-stranded −50 kb lambda viral target DNA on magnetic beads.

| Reaction | Single-stranded Probe DNA | RecA Protein | % Capture of $^{32}$P-Labeled Lambda DNA Target |
|---|---|---|---|
| 1 | lambda | + | 45.9 |
| 2 | lambda | − | 3.7 |
| 3 | φX174* | + | 3.6 |
| 4 | φX174* | − | 3.1 |

*Non-biotinylated, nick-translated RFI

Legend to Table 3: RecA-mediated double D-loop reactions using biotinylated (nick-translated with bio-4-dATP) lambda DNA probes, or non-labeled (nick-translated with dATP) φX174 RFI probes, and $^{32}$P-labeled whole lambda genomic DNA targets were carried out. The single-stranded probes obtained by nick-translation averaged 300–500 bases in size and the lambda DNA probes were all homologous to a contiguous 1000 bp region of the lambda viral genome. RecA-coated ss probes were reacted with lambda target DNA for 1 hr at 37° C., treated with 20 mM EDTA and 0.5M NaCl, and affinity captured on freshly washed streptavidin-coated magnetic DYNABEADS® (Dynal). Non-captured DNA was removed from the reaction mixture by washing. The % of $^{32}$P-labeled lambda DNA remaining on the beads after washing was determined by scintillation counting. Reactions without RecA protein and/or with φX174 DNA sequences as probe, served as controls (see Text and Methods for details). The results show that double D-loop hybrids formed between nick-translated probes and large double-stranded Target DNAs can be specifically captured and detected with magnetic beads.

D. Signal amplification

For The purpose of detecting captured target DNA when the target is not labeled and/or for amplifying signal for detecting low copy number targets, the washed Dynabeads® with attached captured DNA, were washed once in 1× T7 buffer (10× buffer: 400 mM Tris HCl pH 7.5, 100 mM MgCl$_2$, 50 mM DTT) and then resuspended in 44 µl of amplification reaction mix containing 31.1 µl ddH$_2$O, 0.5 µl each of 100 mM dCTP, dGTP and dTTP, 9.4 µl 0.53 mM bio-14-dATP (BRL) and 2 µl 0.8 µM of poly(A) primer SEQ ID NO.4 included bases (without poly (A) tail), are numbers 8001 to 8023 on the lambda genome. The primer, target DNA mixture was then heated to 00° C. for 5 min and cooled to −37° C. for ∼10 min before the following was added; 5 μl 10× T7 buffer, 0.5 μl 13 U/μl T7 SEQUENASE® Version 2.0 (USB), and ddH₂O to a final volume of 50 μl. The reaction was then incubated for 1 hr at 37° C. before being stopped by addition of 5 μl of 0.3M EDTA pH 8.0.

E. Signal detection

Incorporation of bio-14-dATP into primer-synthesized DNA was detected using the SOUTHERN-LIGHT™ (Tropix) chemiluminescence assay. DNA from amplification reactions with and without T7 enzyme were diluted appropriately in TE and 1 μl of DNA mix was added to 4 μl 200 mM NaOH with 12.5 mM EDTA, incubated at room temperature for 5 to 10 min, then spotted onto dry TROPILON-45™ nylon membrane on plastic wrap. DNA spots were air dried, the dried membrane was transferred onto 3 MM CHR (Whatman) chromatography paper and 20× SSC was dropped onto the 3 MM paper around the edges of the nylon. When the DNA dots were wetted, DNA was crosslinked to the membrane with a Stratagene Stratalinker set on "auto". After the nylon was fully wetted by 20× SSC, the SOUTHERN-LIGHT™ (Tropix) biotinylated DNA detection procedure was used with AVIDx-AP™ (alkaline phosphatase; Tropix) and AMPPD substrate, according to the manufacturer's recommended protocol. Chemiluminescence was detected using a Camera Luminometer (Tropix) and Polaroid 612 film. Comparison of results from reactions with and without T7 SEQUENASE® showed that biotin had been incorporated into DNA and was easily detectable by using a chemiluminescence assay. If detection uses an indirect label detection process (i.e., biotin label reacted with AVIDx-AP™ for detection, rather than direct detection of incorporated label, such as FITC) and the detection step is done on beads [DYNABEADS®, Dynal; oligo(dT) beads, Promega], or on a matrix [such as oligo(dT) cellulose, Stratagene POLY(A) QUICK™], the capture matrix must be incubated with some agent to block the non-specific sticking of the detection reagent to the matrix, I-Block reagent mix (Blocking Buffer: SOUTHERN-LIGHT™, Tropix) has been used for this purpose. Washed beads [or oligo(dT) cellulose], with attached DNA were washed 1× in Blocking Buffer then incubated in Blocking Buffer for 10 to 30 min, before washing and addition of AVIDx-AP™ (Tropix). Excess unbound AVIDx-AP™ was then removed by washing according to the Tropix protocol. The capture matrix was then washed with a buffer compatible with substrate detection (Assay Buffer, Tropix can be used for detection by chemiluminescence; alternatively for detection by fluorescence, the ATTOPHOS™ system of JBL Scientific, with its compatible buffers can be used). Substrate is added and the DNA-bound AP is detected by the appropriate means.

It is claimed:

1. A diagnostic method for detecting a linear duplex DNA analyte, having first and second strands, containing a first internal DNA target sequence, comprising providing a set of two DNA probes, having first and second probe strands, where the first and second probe strands (i) contain complementary sequences to the first and second target sequence strands, and (ii) where these complementary sequences also contain complementary overlap between the probe strands, coating the probes with RecA protein in a RecA protein coating reaction, said coating reaction containing a nucleotide cofactor selected from the group consisting of ATPγS, rATP, dATP, and GTPγS, or a mixture of nucleotide cofactors consisting of ATPγS and rATP or ATPγS and ADP, combining the RecA coated probes with the linear duplex DNA, which contains the target sequence, under conditions that produce a probe:target complex containing the probe strands and both target strands, where said complex is stable to deproteinization, and detecting the presence of the probe DNA in the probe:target complex.

2. The method of claim 1, wherein said DNA probes are prepared by nick-translation.

3. The method of claim 1, wherein said cofactor is rATP and said reacting is carried out in the presence or absence of an ATP regenerating system.

4. The method of claim 1, where said cofactor is dATP.

5. The method of claim 1, which further comprises providing a second set of two DNA probes, said probes prepared by nick-translation and having first and second probe strands, complementary to a second duplex target sequence, where the first strand of the probe contains sequences complementary to one strand of the second target sequence and the second strand of the probe contains sequences complementary to the other strand of the second target sequence, where (i) these probes also have a region of complementary overlap to each other, and (ii) the second set of probes does not hybridize to the first set of probes.

6. The method of claim 1, where said coating reaction contains ATP.

7. The method of claim 6, wherein said DNA probes are prepared by nick-translation.

8. A method for isolating a linear duplex DNA analyte, having first and second strands, containing a first internal DNA target sequence, where said duplex DNA analyte is present in a mixture of nucleic acid molecules, comprising providing a set of two DNA probes, having first and second probe strands, where the first and second probe strands (i) contain complementary sequences to the first and second target sequence strands, and (ii) where these complementary sequences also contain complementary overlap between the probe strands, coating the probes with RecA protein in a RecA protein coating reaction, combining the RecA coated probes with the linear duplex DNA, which contains the target sequence, under conditions that produce a probe:target complex containing the probe strands and both target strands, where said complex is stable to deproteinization, separating the probe:target complex from the mixture of nucleic acid molecules, and isolating the duplex DNA analyte containing the target sequence from the probe:target complex.

9. The method of claim 8, wherein said DNA probes are prepared by nick-translation.

10. The method of claim 8, wherein the probes are bound to a solid support.

11. The method of claim 8, wherein said probes contain at least one biotin moiety.

12. The method of claim 11, where said separating is accomplished using streptavidin.

13. The method of claim 12, where the streptavidin is bound to a solid support.

14. The method of claim 8, wherein said isolating further includes heat denaturation of the probe:target complex at a temperature (i) sufficient to release the duplex DNA analyte containing the target sequence from the complex, and (ii) below the melting temperature of the duplex DNA analyte containing the target sequence.

15. The method of claim 14, wherein the duplex DNA analyte is denatured into single-stranded DNA.

16. The method of claim 8, wherein said isolating further includes heat denaturation of the probe:target complex at a temperature (i) sufficient to release the duplex DNA analyte containing the target sequence from the complex, and (ii) at or above the melting temperature of the duplex DNA analyte containing the target sequence.

17. A method for detecting a linear duplex DNA analyte, having first and second strands, containing a first internal DNA target sequence, where said duplex DNA analyte is present in a mixture of nucleic acid molecules, comprising isolating the linear duplex DNA analyte as described in claim 8, wherein said isolating further includes heat denaturation of the probe:target complex at a temperature (i) sufficient to release the duplex DNA analyte containing the target sequence from the complex, and (ii) at or above the melting temperature of the duplex DNA analyte containing the target sequence, adding at least one DNA synthesis primer, which is complementary to the target sequence and has 5' and 3' ends, where said primer does not contain sequences that were present in either of the two DNA probes, and where the detection of the DNA analyte is accomplished by DNA polymerase facilitated primer extension from the 3'-end of the primer, wherein the primer extension is performed in the presence of all four dNTPs and at least one dNTP contains a detectable moiety.

18. The method of claim 17, wherein said DNA probes are prepared by nick-translation.

19. The method of claim 17, wherein said primer strand contains an end terminal extension of DNA that is not complementary to either target strand.

20. The method of claim 17, wherein at least one DNA synthesis primer contains a capture moiety.

21. The method of claim 20, where said detection further includes the generation of primer extension products containing the capture moiety and the detection moiety and said products are isolated using said capture moiety.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 500 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Lambda ( v i i i ) POSITION IN GENOME:
        ( A ) CHROMOSOME/SEGMENT: 500 base pairs
        ( B ) MAP POSITION: 7131 to 7630
        ( C ) UNITS: bp ( x i ) SEQUENCE DESCRIPTION: SEQ ID NO:1:

```
GATGAGTTCG  TGTCCGTACA  ACTGGCGTAA  TCATGGCCCT  TCGGGGCCAT  TGTTTCTCTG      60

TGGAGGAGTC  CATGACGAAA  GATGAACTGA  TTGCCCGTCT  CCGCTCGCTG  GGTGAACAAC     120

TGAACCGTGA  TGTCAGCCTG  ACGGGGACGA  AAGAAGAACT  GGCGCTCCGT  GTGGCAGAGC     180

TGAAAGAGGA  GCTTGATGAC  ACGGATGAAA  CTGCCGGTCA  GGACACCCCT  CTCAGCCGGG     240

AAAATGTGCT  GACCGGACAT  GAAAATGAGG  TGGGATCAGC  GCAGCCGGAT  ACCGTGATTC     300

TGGATACGTC  TGAACTGGTC  ACGGTCGTGG  CACTGGTGAA  GCTGCATACT  GATGCACTTC     360

ACGCCACGCG  GGATGAACCT  GTGGCATTTG  TGCTGCCGGG  AACGGCGTTT  CGTGTCTCTG     420

CCGGTGTGGC  AGCCGAAATG  ACAGAGCGCG  GCCTGGCCAG  AATGCAATAA  CGGGAGGCGC     480
```

TGTGGCTGAT TTCGATAACC                                                                                    500

( 2 ) INFORMATION FOR SEQ ID NO:2:

( i ) SEQUENCE CHARACTERISTICS:
    ( A ) LENGTH: 4 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( C ) INDIVIDUAL ISOLATE: Cleavage site for Dpn I ( x i ) SEQUENCE DESCRIPTION: SEQ ID NO:2:

GATC                                                                                                       4

( 2 ) INFORMATION FOR SEQ ID NO:3:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: lambda
    ( C ) INDIVIDUAL ISOLATE: PCR primer from lambda genome ( v i i i ) POSITION IN GENOME:
    ( B ) MAP POSITION: 6631 to 6655
    ( C ) UNITS: bp ( x i ) SEQUENCE DESCRIPTION: SEQ ID NO:3:

GCGGCACGGA GTGGAGCAAG CGTGA                                                                               25

( 2 ) INFORMATION FOR SEQ ID NO:4:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: lambda
    ( C ) INDIVIDUAL ISOLATE: polyA construct from lambda genome ( v i i i ) POSITION IN GENOME:
    ( B ) MAP POSITION: 8001-8023
    ( C ) UNITS: bp ( x i ) SEQUENCE DESCRIPTION: SEQ ID NO:4:

AAAAAAAAAA AAAAAATACG GCTGAGGTTT TCAACGGC                                                                  38